United States Patent [19]
Furukawa et al.

[11] Patent Number: 5,730,701
[45] Date of Patent: Mar. 24, 1998

[54] ENDOSCOPE

[75] Inventors: Tatsuya Furukawa; Yoshihiro Iida; Koji Nakamoto, all of Hachioji, Japan

[73] Assignee: Olympus Optical Co., Ltd., Tokyo, Japan

[21] Appl. No.: 601,119

[22] Filed: Feb. 14, 1996

[30] Foreign Application Priority Data

Sep. 12, 1995 [JP] Japan ................................. 7-234487
Sep. 13, 1995 [JP] Japan ................................. 7-235717

[51] Int. Cl.$^6$ ............................................. A61B 1/04
[52] U.S. Cl. .......................... 600/127; 600/121; 600/129
[58] Field of Search ................................ 600/121, 122, 600/123, 124, 125, 127, 129; 403/300, 306, 308, DIG. 4

[56] References Cited

FOREIGN PATENT DOCUMENTS

| | | |
|---|---|---|
| 2-25361 | 7/1990 | Japan . |
| 614865 | 1/1994 | Japan ........................... 600/127 |
| 7-184838 | 7/1995 | Japan . |

*Primary Examiner*—Beverly M. Flanagan
*Attorney, Agent, or Firm*—Morgan, Lewis & Bockius LLP

[57] ABSTRACT

A tip ring 18 for forming a lock mechanism for locking a tip cover 51 is formed in a circumferential part with a lock projection 22 for forming a lock groove 26 which becomes a recess of the lock mechanism on the endoscope tip side between the lock projection and curved rubber 19. A lock piece which becomes a projection of the lock mechanism of the tip cover 51 is locked into the lock groove 26 made by disposing the tip ring 18 and the curved rubber 19. To enhance the attachment property of the lock piece 52 to the lock groove 26, the lock projection 22 is formed with a slant projection 27 which becomes a slope for guiding the lock piece 52 to the lock groove 26. The slant projection 27 is formed as a slope projecting to the tip side from the lock projection 22 and rising from the tip bottom face to the top face of the lock projection 22.

27 Claims, 22 Drawing Sheets

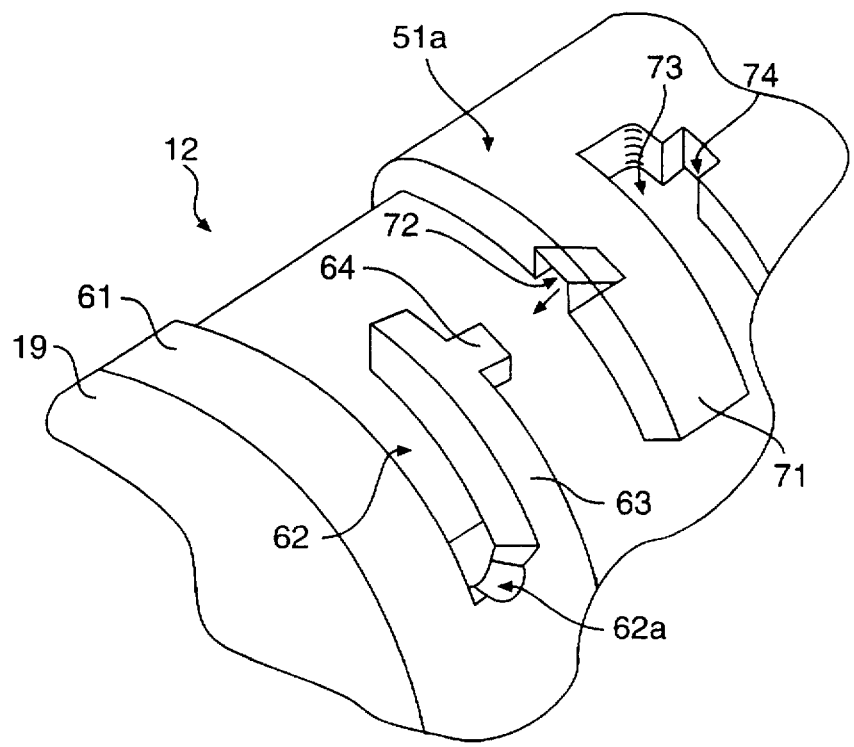
FIG. 9
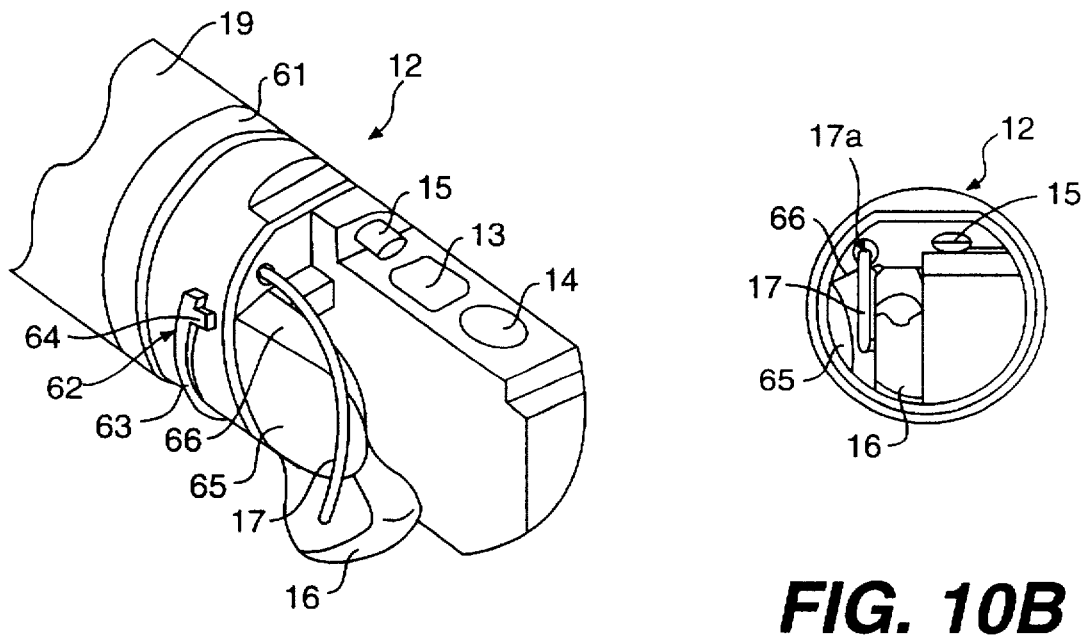
FIG. 10A
FIG. 10B

ENDOSCOPE

BACKGROUND OF THE INVENTION

1. Field of the Invention

The present invention relates generally to an endoscope having a tip and section to which a tip cover is attached and, more particularly, the invention relates to an improved detachable tip cover and an improved structure for attaching a tip cover to a tip section of an endoscope.

2. Related Art

As generally known, a medical endoscope such as a gastroscope or a duodenal scope is provided with an insertion section which is inserted into the abdominal cavity of a patient for observing or treating the affected part of the patient. Some endoscopes are provided with a treatment tool raising affected part when a living body test tissue is collected or treated with a treatment tool such as forceps while the affected part is being observed with the endoscope.

The treatment tool raising device basically consists of a treatment tool raising stand pivotable on a raising shaft disposed on the endoscope tip end section and a manipulation wire coupled to the treatment tool raising stand. The manipulation wire is advanced or retracted with a manipulation part disposed on the operator's side, thereby properly adjusting the angle of the treatment tool raising stand for orienting the forceps in a desired direction.

When the endoscope is used, the tip end section and insertion section of the endoscope are inserted into the abdominal cavity and come in contact with body fluid, thus the body fluid comes in contact with the raising shaft on the treatment tool raising stand, a slide part with the tip component part, a fit part disposed between a manipulation wire fixing member connected to the end of the manipulation wire and the treatment tool raising stand, etc. Therefore, after the endoscope is used, the parts of which must be washed to prevent infections, etc. However, since the treatment tool raising device has a number of fine members such as the manipulation wire fixing member and the raising shaft, washing of the endoscope parts takes very much time and effort.

To solve the problem, an endoscope of tip cover detachment type comprising an insertion section having a tip hard part consisting of a main body and a tip cover detachable/attachable from/to the main body is disclosed in Japanese Utility Model Publication No. Hei 2-25361. The detachable tip cover becomes severely dirty and must be replaced for each case. However, the structure as in the conventional art allows the tip cover to be reused; it is feared that a used tip cover not sufficiently sterilized or washed may be reused in error.

Even if the plastic tip cover is sufficiently disinfected and sterilized, while it is used more than once, the fit part strength lowers and it is feared that the tip cover may fall off during the case.

Further, since it is a detachable/attachable tip cover, it needs to be easily removed. However, with the endoscope having a detachment-type tip cover (tip cap) as disclosed in Japanese Utility Model Publication No. Hei 2-25361, if the attachment property of the tip cover to the endoscope tip end section takes precedence when the tip cover is made a detachment-type structure, the tip cover becomes easy to detach from the endoscope tip end section. In contrast, if the tip cover is made hard to detach from the endoscope tip end section, the attachment property of the tip cover to the endoscope tip end section worsens.

On the other hand, the present applicant has proposed a tip cover with a detachment-type forceps raising stand in Unpublished Japanese Patent Application No. Hei 5-333219, wherein when the tip cover and endoscope tip end section are attached, the entire tip end section side of an engagement part formed in the endoscope tip end section with which the tip cover comes in contact is formed with a slant part for improving the attachment property. However, as shown in FIG. 32, if the entire tip end section side of an engagement part 102 of the endoscope tip end section 101 is formed with a slant part 103, when a tip cover 104 is attached to the endoscope tip and section 101, circumferential recesses 105 are formed by the slope of the slant part 103 between the tip cover 104 and the engagement part 102, whereby the insertion property into an abdominal cavity lowers.

As shown in FIG. 33, with an endoscope 110 from which a tip cover is removed, at the washing time, a forceps stand 111 is depressed downward from a tip component part 112 with a finger for exposure and the surroundings of the forceps stand are washed. However, when the forceps stand 111 is depressed downward from the tip component part 112, it is feared that a manipulation wire 113 may enter the space between the internal face of a forceps stand guide wall 114 and the forceps stand 111. Thus, an endoscope wherein the manipulation wire 113 does not enter the space between the forceps stand 111 and the internal face of the forceps stand guide wall 114 is desired.

SUMMARY OF THE INVENTION

It is therefore an object of the invention to provide an endoscope from which a tip cover can be easily removed with no fear of reuse of a used tip cover.

It is another object of the invention to provide an endoscope which is good in attachment property of a tip cover to an endoscope tip end section, excellent in insertion property without any step on the outer surface of the attachment part between the tip cover and the endoscope tip end section when the tip cover is attached to the endoscope tip end section, and has a lock mechanism for preventing the tip cover from falling out from the endoscope tip end section.

According to the invention, the endoscope has the detachable tip cover that can be attached to the tip component part by locking the lock pieces disposed in the endoscope tip cover in the grooves made in the tip component part of the endoscope. When the tip cover is removed from the tip component part, it can be easily removed with a removal jig for plastic deformation such as bending the lock pieces. Since the lock pieces are plastically deformed, the removed tip cover cannot again be used.

According to another aspect of the invention, the endoscope includes an endoscope tip end section, a tip cover attached to the endoscope tip end section, and a lock mechanism provided by a pair of recess and a projection for integrally lock the endoscope tip end section and the tip cover, wherein a slope is made in a part of at least one of the recess and the projection making up the lock mechanism.

According to the structure of the endoscope of the invention, the slope is made in a part of at least one of the recess and the projection making up the lock mechanism, whereby when the tip cover is attached to the endoscope tip end section, it can be easily attached to the endoscope tip end section with the lock strength provided.

BRIEF DESCRIPTION OF THE DRAWING

In the accompanying drawings:

FIG. 9 is a perspective view showing an endoscope with the tip cover side formed with a slant part for improving the attachment property of a tip cover to a tip component part according to a second embodiment of the invention;

FIG. 10A is a perspective view showing another structure of wire entry prevention means, and FIG. 10B is a sectional view of an endoscope tip end section;

FIG. 21 is a drawing showing a molded part of the tip end section of a light guide fiber in the fourth embodiment of the invention.

DESCRIPTION OF THE PREFERRED EMBODIMENTS

Preferred embodiments of the invention will now be described in detail with reference to the accompanying drawings.

Figure 1:
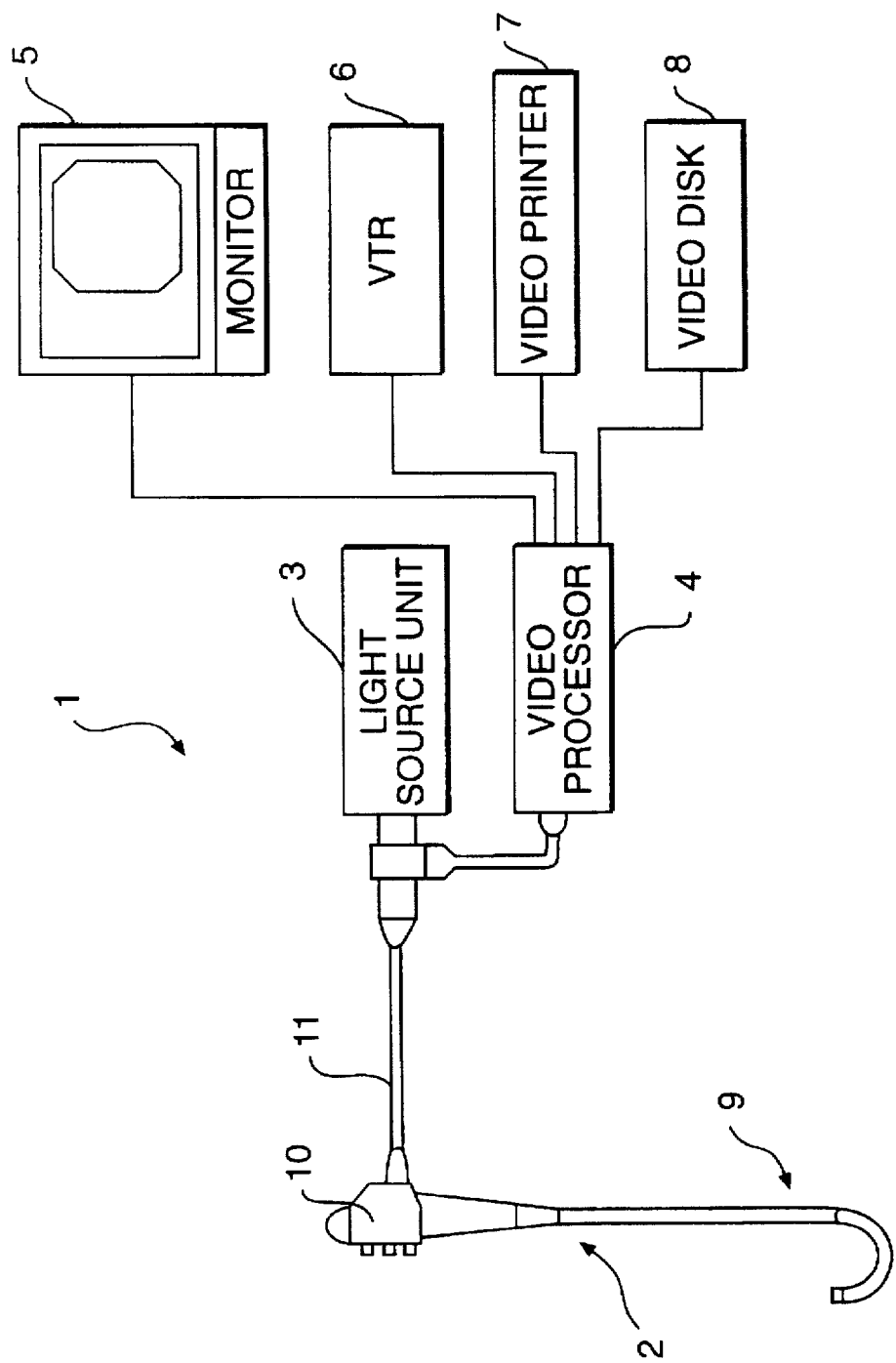
FIG. 1 is an illustration showing a schematic configuration of an endoscope system according to a first embodiment of the invention.
Figure 2:
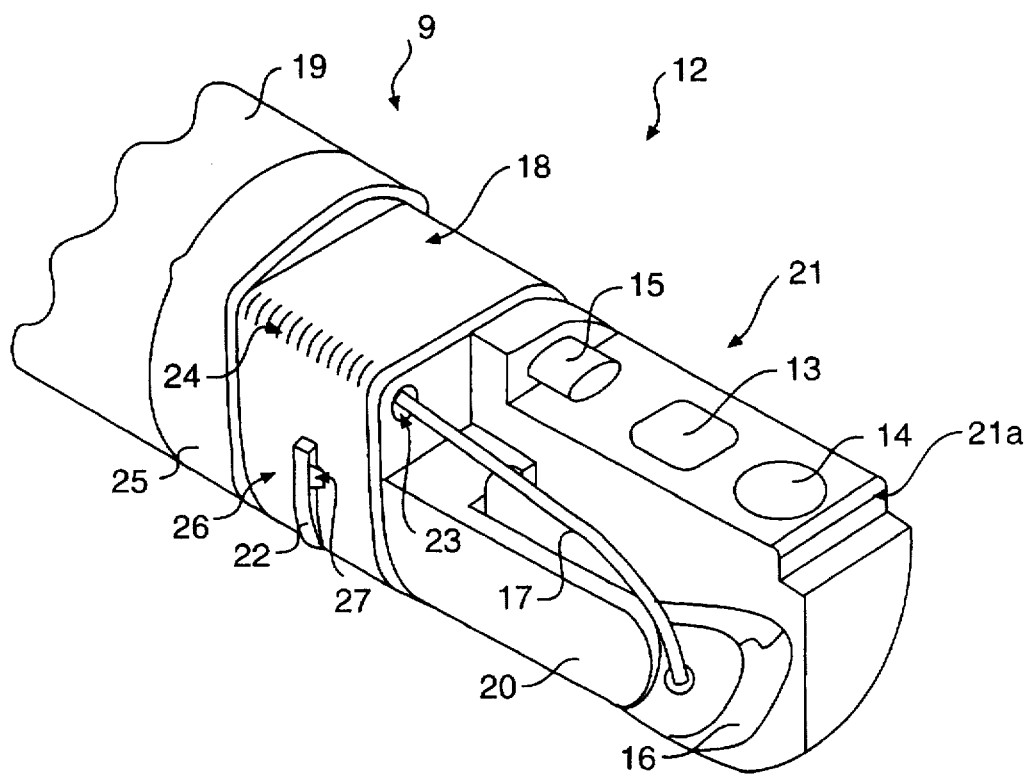
FIG. 2 is a perspective view showing a tip component part formed with a slant part for improving the attachment property of a tip cover to the tip component part according to the first embodiment of the invention.
Figure 3:
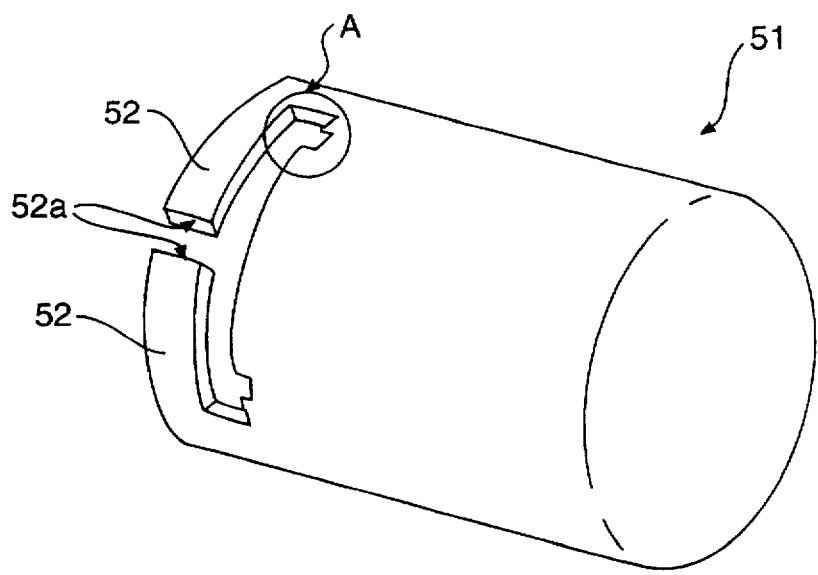
FIG. 3 is a perspective view showing the tip cover formed with lock pieces according to the first embodiment of the invention.
Figure 4:
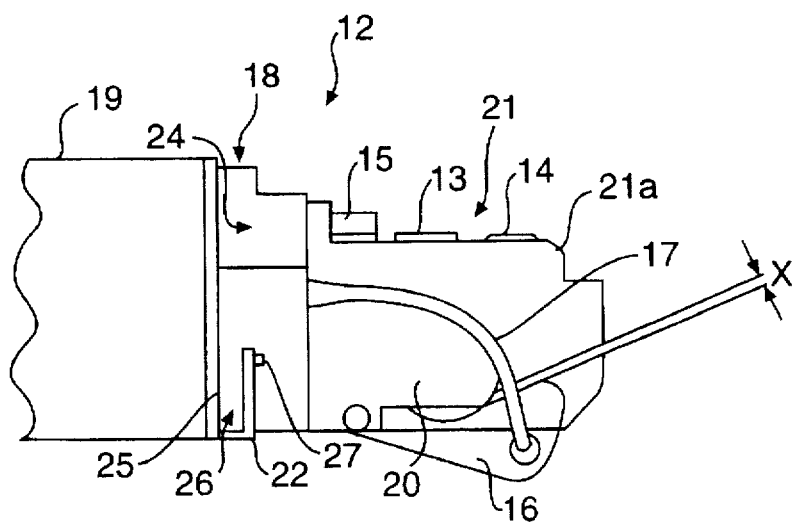
FIG. 4 is an illustration showing a state in which a forceps stand of the endoscope tip end section is depressed according to the first embodiment of the invention.
Figure 5A:
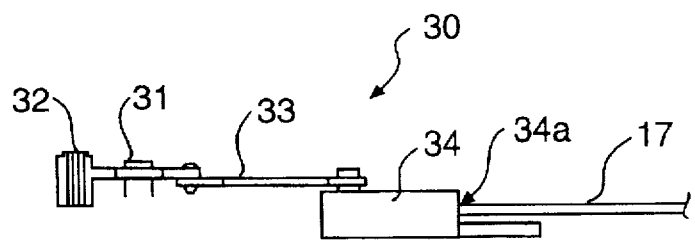
FIG. 5A is a top view illustrating a schematic structure of a forceps stand manipulation unit according to the first embodiment of the invention.
Figure 5B:
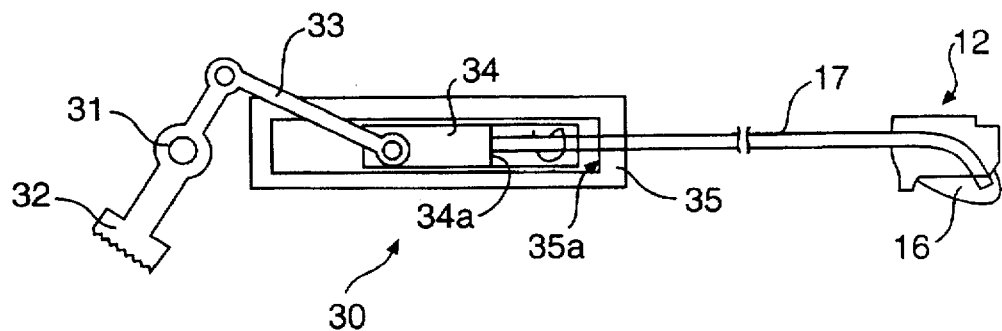
FIG. 5B is a side view of the forcept stand manipulation unit.
Figure 6:
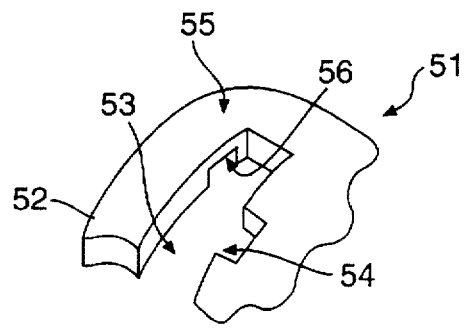
FIG. 6 is an enlarged view of part A in FIG. 3.
Figure 7:
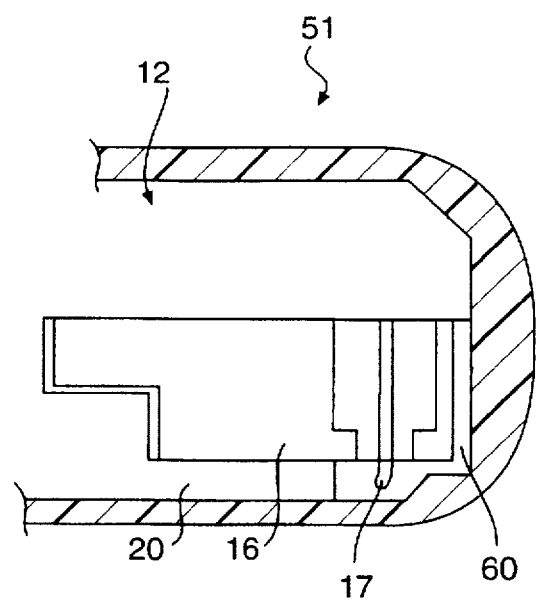
FIG. 7 is an illustration showing a relief part when the tip cover is attached to the tip component part according to the first embodiment of the invention.
Figure 8:
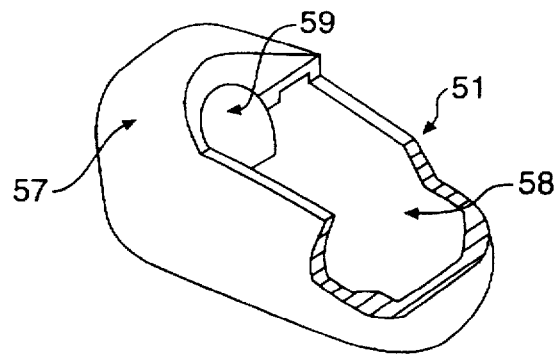
FIG. 8 is a perspective view partially in cross section when the tip cover is viewed from a window according to the first embodiment of the invention.

First embodiment:

FIG. 1 is an illustration showing a schematic configuration of an endoscope system according to a first embodiment of the invention. FIG. 2 is a perspective view showing a tip component part formed with a slant part for improving the attachment property of a tip cover to the tip component part according to the first embodiment of the invention. FIG. 3 is a perspective view showing the tip cover formed with lock pieces according to the first embodiment of the invention. FIG. 4 is an illustration showing a state in which a forceps stand of the endoscope tip end section is depressed according to the first embodiment of the invention. FIG. 5A is a top view showing a schematic structure of a forceps stand manipulation unit according to the first embodiment of the invention, and FIG. 5B is a side view of the forceps stand manipulation unit. FIG. 6 is an enlarged view of part A in FIG. 3. FIG. 7 is an illustration showing a relief part when the tip cover is attached to the tip component part according to the first embodiment of the invention. FIG. 8 is a perspective view partially in cross section when the tip cover is viewed from a window according to the first embodiment of the invention.

As shown in FIG. 1, an endoscope system 1 includes an endoscope 2 containing a solid state image sensor (not shown), a light source unit 3 for supplying illuminating light to the tip end section of the endoscope 2, a video processor 4 having signal processing means for processing an electric signal transmitted from image pickup devices of the endoscope 2 to produce a video signal, a monitor 5 for displaying a subject image provided by the video signal produced by the video processor 4, a VTR 6 for recording and reproducing the video signal, a video printer 7 for printing the subject image displayed on the monitor 5, a video disk 8 of a mass storage device for recording the video signal, etc.

The endoscope 2 comprises an insertion section 5 inserted into an abdominal cavity, a manipulation part 10 positioned behind the insertion section 9, and a universal cord 11 extending from the side of the manipulation part 10.

As shown in FIG. 2, an endoscope tip end section 12 positioned on the tip end section side of the insertion section 9 of the endoscope 2 has a tip component part 21 wherein components are disposed such as an object lens 13 for observing an affected part, an illumination lens 14 for illuminating the inside of the abdominal cavity such as the affected part, a nozzle 15 for sending a cleaning liquid for cleaning filth, body fluid, etc., deposited on the object lens 13 and the illumination lens 14 and air for blowing off water drops, etc., deposited on the lenses 13 and 14, a forceps stand 16 for supporting a treatment tool (now shown) inserted into the endoscope and projecting from the endoscope tip end section, a manipulation wire 17 connected at one end to the forceps stand 16 and coupled at the other end to a forceps stand manipulation unit (described below) located in the manipulation part 10 of the endoscope 2, a lock ring 18 for forming a lock mechanism for locking a tip cover (described below), curved rubber 19 for covering a curved part comprising a plurality of curved frames jointed to each other (not shown) and covered with the rear end of the lock ring 18, and forceps stand guide wall 20 for preventing the forceps stand 16 from being out of place in an outer peripheral surface direction perpendicular to a rotation direction of the forceps stand 16 when the forceps stand 16 is rotated by pulling the manipulation wire 17. A top cover 51 shown in FIG. 3 is attached to the tip component part 21.

Each edge part of the tip component part 21 is chamfered as indicated by reference numeral ad for preventing injury to operator's fingers, etc., by the edges of the airiest parts when the tip cover is not attached.

First, the lock mechanism on the endoscope tip end section side will be discussed.

As shown in FIG. 2, the tip ring 18 for forming the lock mechanism for locking the tip cover 51 is formed of a material having living body compatibility, such as polysulfone, and is bonded and fixed integrally to the tip component part 21 with an adhesive having living body compatibility.

The tip ring 18 is formed in a circumferential part with a lock projection 22 for forming a lock groove 26 which becomes a recess of the lock mechanism on the endoscope tip side.

That is, the lock groove 26 which becomes the recess of the lock mechanism on the endoscope tip side is formed between the lock projection 22 and a butt part 25. A lock piece 52 which becomes a projection of a locked mechanism (described below) of the tip cover 51 shown in FIG. 3 is locked into the lock groove 26.

To improve the attachment property of the lock piece 52 of the tip cover 51 to the lock groove 26, the lock projection 22 is formed with a slant projection 27 which becomes a slant part for guiding the lock piece 52 of the tip cover 51 to the lock groove 26. The slant projection 27 is formed projecting from the lock projection 22 to the endoscope tip end section side so as to first abut the lock piece 52 when the lock piece 52 is locked into the lock groove 26.

The slant projection 27 is formed as a slope rising from the lower face of the tip end section side to the upper face of the lock projection 22 so as to allow the lock piece 52 of the tip cover 51 to the lock groove 26, the lock be locked into the lock groove 26. It is desirable to make the slant projection 22 5 mm or less wide.

The outer dimensions of the lock projection 22 are made substantially the same as or slightly larger than those of the tip cover 51. The lock ring 18 is formed with an oddly shaped part 24 for providing thickness in exit proximity 23 of the manipulation wire 17.

The minimum thickness of the lock ring 18 is suppressed to about 0.3 mm having resistance for preventing peel by repeating attachment of the tip cover 51, so that the lock ring 18 has sufficient strength although it is thin. The lock ring 18 is colored a different color from the tip cover 51 so as to enable an easy distinction between the tip cover 51 and the lock ring 18 when the tip cover 51 is attached to the tip component part 21. Further, the outer dimensions of the butt part 25 disposed at the curved rubber 19 are substantially the same as those of the lock ring 18.

On the other hand, as shown in FIG. 4, the forceps stand 16 is depressed downward from the tip component part 2: with a finer at washing; to prevent damage to the manipulation wire 17 entering the space between the inner face of the forceps stand 16 stops without opening a gap x between the forceps stand 16 and the forceps stand guide wall 20 more than the diameter of the manipulation wire 17.

To stop the forceps stand 16 at a position where the gap x does not open more than the diameter of the manipulation wire 17, a forceps stand manipulation unit 30 is provided with wire entry prevention means as shown in FIGS. 5A and 5B.

That is, as shown here, the forceps stand manipulation unit 30 for rotating the forceps stand 16 consists mainly of a manipulation knob 32 located in the manipulation part 10 rotating on a shaft 31, a couple bar 33 couple to the manipulation knob 32, a push/pull part 34 for rotating the forceps stand 16 by advancing and retracting the manipulation wire 17 connected to the couple bar 33, and a guide 35 for regulating the push/pull part 34 so as to move it in the longitudinal direction of the endoscope.

The guide 35 is disposed in parallel with the longitudinal direction of the endoscope so as to surround the push/pull part 34. The push/pull part 34 moves in the tip direction, whereby a step part 34a located in the push/pull part 34 abuts a tip side wall 35a of the guide 35. That is, the gap x is prevented from opening more than the diameter of the manipulation wire 17 by setting the travel distance of the manipulation wire 17 until the push/pull part 34 abuts the tip side wall 35a of the guide 35 as the wire entry prevention means.

Next, the locked mechanism of the tip cover 51 will be discussed.

As shown in FIG. 3, the tip cover 51 attached to the tip component part 21 including the lock groove 26 defined by the lock projection 22 of the lock ring 18 and the butt part 25 is formed with two lock pieces 52 having elasticity for overriding the lock projection 22 of the tip component part 21 and being locked into the lock groove 26.

the lock piece 52 has an outer form having the length and width dimensions substantially the same as or smaller than those of the lock groove 26 so as to fit in the lock groove 26.

If the lock piece 52 projects from other portions of the tip cover 51 when it is locked into the lock groove 26, it is feared that when the projecting lock piece 52 is caught in something when the endoscope with the tip cover 51 attached to the tip component part 21 is inserted into an abdominal cavity, it may be pulled and detached from the lock groove 26 and the tip cover 51 may fall out from the tip component part 21. Thus, the outer dimensions of the lock piece 52 are set the same as those of other portions of the tip cover 52 or to the dimensions not projecting therefrom and also the same as those of the lock projection 22 of the tip component part 21 or to the dimensions not projecting therefrom.

To provide the lock piece 52 for the tip cover 51, the tip cover 51 is formed with a slit 53. To fit without any gap the lock projection 22 disposed in the tip component part 21, the slit 53 is formed with a recess 54 for fitting the slant projection 27 made in the lock projection 22 at a position corresponding to the slant projection 27 made in the lock projection 22, a shown in FIG. 6. The length and width dimensions of the slit 53 are set substantially the same as or slightly larger than those of the lock projection 22. Disposed on the inner peripheral surfaces side of root proximity 55 of the lock piece 52 is a hinge 56 having a part formed as a predetermined thickness for providing desired bending strength (elastic force) for the lock piece 52.

On the other hand, as shown in FIG. 7, the inner face of the tip cover 51 is formed with a relief part 60 so that a part of the forceps stand 16 and the inner face of the tip cover 51 do not strike each other when the tip cover 51 is attached to the tip component part 21.

As shown in FIG. 8, the tip cover 51 is formed with a deformed part 57 so as to correspond to the oddly shaped part 24 of the tip component part 21 and a window 58 to which the object lens 13, the illumination lens 14, and the forceps stand 16 located in the tip component part 21 are opposed.

The window 58 is formed at the rear end with an insulation part 59 for preventing a short between a high-frequency treatment tool (not shown) and the tip component part 21 when the high-frequency treatment tool is used. The lock piece 52 is made 1 mm or more wide and 0.5 mm or more thick to ensure the lock strength of the lock piece 52 for the lock projection 22. Further, ends 52a of the lock pieces 52 are formed at the same angle in the range of 45° to 90° with the outer peripheral surface. Although a plurality of lock pieces 52 are provided in the embodiment, only one lock piece may be provided. Further, the lock projection 22 and the slit 53 are formed so as to project almost perpendicularly to the peripheral surface to enhance the lock strength of the lock projection 22 and the slit 53.

Attachment of the tip cover 51 having the structure as described above to the tip component part 21 will be discussed.

To attach the tip cover 51 to the tip component part 21, namely, the endoscope tip end section 12, first the face of the tip component part 21 on which the object lens 13 and the illuminating lens 14 are disposed is matched with the window 58 of the tip cover 51 in orientation. The tip cover 51 is inserted gradually in the longitudinal direction of the tip component part 21. Then, the tip end section side end face of the lock piece 51 made in the tip cover 51 abuts the slope of the slant projection 27 made at the lock projection 22 of the tip component part 21.

As the tip cover 51 is furthermore inserted into the tip component part 21, the lock pieces 52 move along the slope of the slant projection 27. Since the slant projection 27 is situated on the root sides of the lock pieces 52, the almost entire lock pieces 52 are lifted up and since the hinges 56 are located at the root proximity 55 of the lock pieces 52, the lock pieces 52 are bent so as to be lifted up in the outer peripheral direction perpendicular to the longitudinal direction, whereby the attachment property is enhanced.

Further, the tip cover 51 is pushed. Then, the lock pieces 52 climb over the lock projection 22 and are fitted in the lock groove 26 by a restoration force of the hinges 56 and the oddly shaped part 24 of the tip component part 21 and the deformed part 57 of the tip cover 51 are fitted. The attachment of the tip cover 51 to tip component part 21 is now complete.

To clean the surroundings of the forceps stand after the test ends, the manipulation knob 32 is fully turned to put down the forceps stand 16, then the parts such as the forceps stand 16 and the tip component part 21 are cleaned in running water with a brush and rinsed, then disinfected.

Since a part of the lock projection is formed with the slant projection for guiding the lock pieces to the lock groove, when the tip cover is pushed into the tip component part for attachment, the lock pieces can be made to climb over the lock projection while they are lifted up from the root proximity, and can be locked into the lock groove, whereby the tip cover can be smoothly attached to the endoscope tip end section simply by pushing it into the tip component part.

Figure 15:
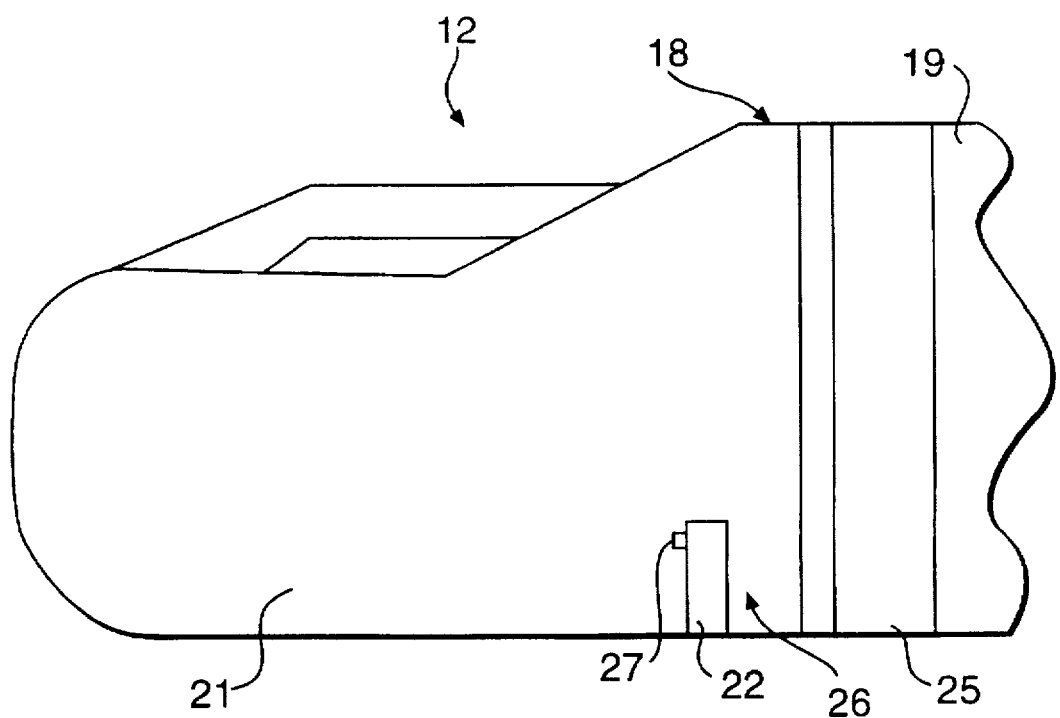
FIG. 15 is a side view showing the endoscope tip end section in the first embodiment.

While the outer dimensions of the lock piece are set the same as those of the tip cover and those of the lock projection or to the dimensions not projecting therefrom, the length and width dimensions of the lock piece are made substantially the same as or slightly smaller than those of the lock groove and the length and width dimensions of the slit are made substantially the same as or slightly larger than those of the lock projection, whereby when the tip cover is attached to the endoscope tip end section, as shown in FIG. 15, projection of only the lock piece or a recess in the outer surface can be removed, whereby the endoscope to which the tip cover is attached can be smoothly inserted into the abdominal cavity.

Further, the hinges are located at the root proximity of the lock pieces for providing a desired elastic force for the lock pieces, whereby the lock pieces are bent smoothly in the outer peripheral direction perpendicular to the longitudinal direction of the lock pieces, so that the attachment property of the tip cover is drastically enhanced.

The tip cover is formed with the deformed part so as to correspond to the oddly shaped part made in the tip component part, whereby when the tip cover is attached to the tip component part, it can be prevented from turning relative to the tip component part.

Further, since the travel distance of the manipulation wire until the push/pull part abuts the tip side wall of the guide is set so that the gap between the forceps stand and the forceps stand guide wall does not open more than the diameter of the manipulation wire, the manipulation wire can be prevented from entering the inside of the forceps stand guide wall, thereby eliminating manipulation wire engagement caused by the manipulation wire entering the space between the forceps stand and the forceps stand guide wall.

The inner face of the tip cover is formed with a relief part for preventing contact with the forceps stand, whereby a chamfer R made in the tip of the tip cover can be largely set, so that safety of the endoscope to which the tip cover is attached and the insertion property into the abdominal cavity can be improved drastically.

The tip cover is made compatible with other types of endoscopes for common use, whereby inexpensive tip covers can be provided.

Second embodiment:

FIG. 9 is a perspective view showing an endoscope with the tip cover side formed with a slant part for improving the attachment property of a tip cover to a tip component part according to a second embodiment of the invention.

Although the endoscope of the first embodiment has the lock projection on the tip component part side formed with the slant part for improving the attachment property of the tip cover to the tip component part, the tip cover side is formed with the slant part for improving the attachment property of the tip cover to the tip component part in the second embodiment.

That is, as shown in FIG. 9, a lock ring 61 on the side of an endoscope tip end section 12 is formed with a lock groove 62 and a lock projection 63 as the lock side. A projection 64 projecting toward the tip side in the longitudinal direction is made at the tip proximity of the lock projection 63.

On the other hand, a lock piece 71 on the locked side of a tip cover 51a is formed with a slant recess 72 used as the slant part for improving the attachment property of the tip cover 51a to the endoscope tip end section 12 at a position corresponding to the projection 64. The slant recess 72 is formed as a slope declining from the top face side of the lock ring 61 side toward the bottom face direction of the lock piece 71.

A slit 73 for housing the lock projection 63 in the tip cover 51a without any gap is made to form the tip cover 51a with the lock piece 71. The slit 73 is formed with a recess 74 for housing the projection 64. Numeral 62a is a removal groove for inserting a removal jig such as a pick (not shown) when the tip cover 51a is removed from a tip component part 21. Other parts are similar to those of the first embodiment; parts identical with to those previously described in the first embodiment are denoted by the same reference numerals in the second embodiment and will not be discussed again.

In the second embodiment, when the tip cover 51a is attached to the tip component part 21, first it is inserted in the longitudinal direction of the tip component part 21. Then, the slope of the slant recess 72 made in the lock piece 71 abuts the projection 74 projecting to the tip side of the lock projection 63 forming a part of the endoscope tip end section 12.

As the tip cover 51a if furthermore pushed, the slope of the lock piece 71 moves so as to be pushed up along the upper edge on the tip side of the projection 64 and the entire lock piece 71 is pushed up in the outer peripheral direction perpendicular to the longitudinal direction.

The tip cover 51a is furthermore pushed. Then, the lock piece 71 climbs over the lock projection 63 and fits in the lock groove 62 and the projection 64 fits in the recess 74, making the outer surface almost even. The attachment of the tip cover 51a to the tip component part 21 is now complete.

Thus, the slant recess used as the slant part for improving the attachment property of the tip cover to the tip component part is made in the inner peripheral surface of the lock piece of the tip cover, thereby eliminating a recess in the outer surface occurring between the tip cover and the tip component part when the tip cover is attached to the tip component part, thereby furthermore improving the insertion property of the endoscope to which the tip cover is attached into the abdominal cavity.

The projection made at the lock projection fits securely and integrally in the recess made in the slit and the circumferential lock strength is enhanced, thus preventing the tip cover from turning relative to the tip component part. Thus, the tip component part and the tip cover may be shaped like a circle without making an oddly shaped part in the tip component part or a deformed part in the tip cover.

Further, since the projection of the lock projection is located at the root proximity relative to the lock piece, when the tip cover is attached, the entire lock piece can be pushed up smoothly in the outer peripheral direction perpendicular to the longitudinal direction. Other functions and effects are similar to those of the first embodiment.

By the way, to clean the endoscope tip end section from which the tip cover is removed, the gap between the forceps stand and the forceps stand guide wall is set so as not to open more than the diameter of the manipulation wire to prevent the manipulation wire form entering the gap between the forceps stand and the forceps stand guide wall when the forceps stand is depressed in the first embodiment. Thus, the rotation range of the forceps stand is regulated and the space between the forceps stand side face and the forceps stand guide wall and the tip component part may be unable to be cleaned sufficiently. Thus, an endoscope allowing a forceps stand to be rotated to the lower side of a tip component part at the cleaning time is desired.

As shown in FIGS. 10A and 10B, in the endoscope of the embodiment, a slope 66 slanting toward the lower part of the outer peripheral surface from just below an exit 17a of a manipulation wire 17 is made on a forceps stand guide wall 65 of the tip component part 21 provided with an object lens 13, an illumination lens 14, a nozzle 15, a forceps stand 16, the manipulation wire 17, etc.

Thus, to clean the surroundings of the forceps stand 16 and the tip component part 21, the manipulation wire 17 is supported with fingers and is moved along the slope 66 to the outer peripheral face side of the forceps stand guide wall 65. The forceps stand 16 is depressed with fingers and positioned lower than the tip component part 21, improving the cleaning property.

The slope slanting toward the lower part of the outer peripheral surface from just below the exit of the manipulation wire is made on the forceps stand guide wall, whereby the manipulation wire is moved to the outer peripheral face side of the forceps stand guide wall and is positioned lower than the tip component part, thereby drastically improving the cleaning workability. Since the manipulation wire is moved to the outer peripheral face side of the forceps stand guide wall, manipulation wire engagement between the forceps stand and the forceps stand guide wall can be prevented.

Figure 11:
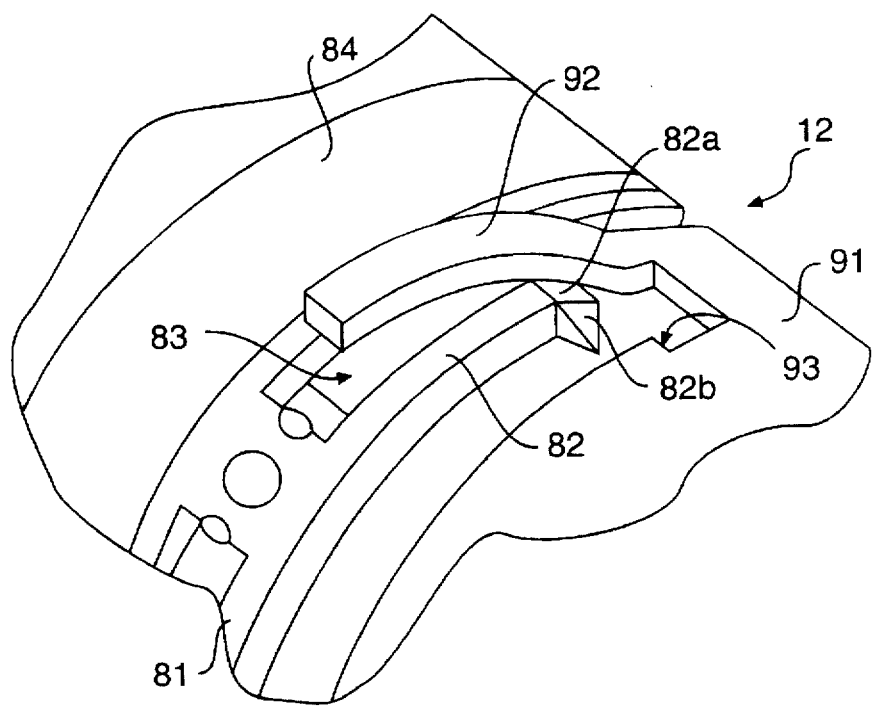
FIG. 11 is a perspective view showing an endoscope with the tip component part side formed with a slant part for improving the attachment property of a tip cover to a tip component part according to a third embodiment of the invention.

Third Embodiment:

FIG. 11 is a perspective view showing an endoscope with the tip component part side formed with a slant part for improving the attachment property of a tip cover to a tip component part according to a third embodiment of the invention.

As shown in the figure, in the embodiment, a first slope 82a part and a second slope part 82b used as slant parts for improving the attachment property of the tip cover to the tip component part are made on the circumferential face and longitudinal direction tip side face of the tip of a lock projection 82 made at a lock ring 81.

That is, to smoothly lock a lock piece 92 of locked means disposed in a tip cover 91 into a lock groove 83 made in the lock ring 81, the tip of the lock projection 82 is formed with the first slope part 82a having a slope descending toward the inner peripheral surface side as it goes in the tip direction and the second slope part 82b having a slope projecting from the first slope part 82a to the longitudinal direction tip side and rising from the tip side bottom face to the top face of the first slope part 82a.

The tip cover 91 is formed with a recess 93 in which the second slope part 82b fits on the root side. Curved rubber 84 is coupled to a rear end 58 of the lock ring 81.

First, when the tip cover 91 is attached to the endoscope tip end section, it is inserted in the longitudinal direction of a tip component part 21. Then, the lock piece 92 abuts the second slope part 82b projecting toward the tip side at the tip of the lock projection 82 forming a part of the endoscope tip end section.

As the tip cover 91 is furthermore pushed, the lock piece 92 moves along the slope of the second slope part 82b and lifts up in the outer peripheral direction perpendicular to the longitudinal direction. When the tip cover 91 is furthermore pushed, the lock piece 92 is placed on the slope of the firs slope part 82a and is pushed up in the outer peripheral direction perpendicular to the longitudinal axis.

The tip cover 91 is furthermore pushed. Then, the lock piece 92 climbs over the lock projection 82 and fits in the lock groove 83 and the second slope part 82b fits in the recess 93. The attachment of the tip cover 91 is now complete.

Thus, the first and second slope parts used as the slant parts are made on the tip side of the lock projection, the lock piece of the tip cover can move on the second slope part and the first slope part in order, can be smoothly pushed up in the outer peripheral direction perpendicular to the longitudinal axis, and can be locked into the lock groove.

The slant parts for pushing up the lock piece are made up of the first and second slope parts, whereby the slope of each slope part can be set small, so that when the tip cover is attached, asperities on the outer surface can be lessened.

Figure 12:
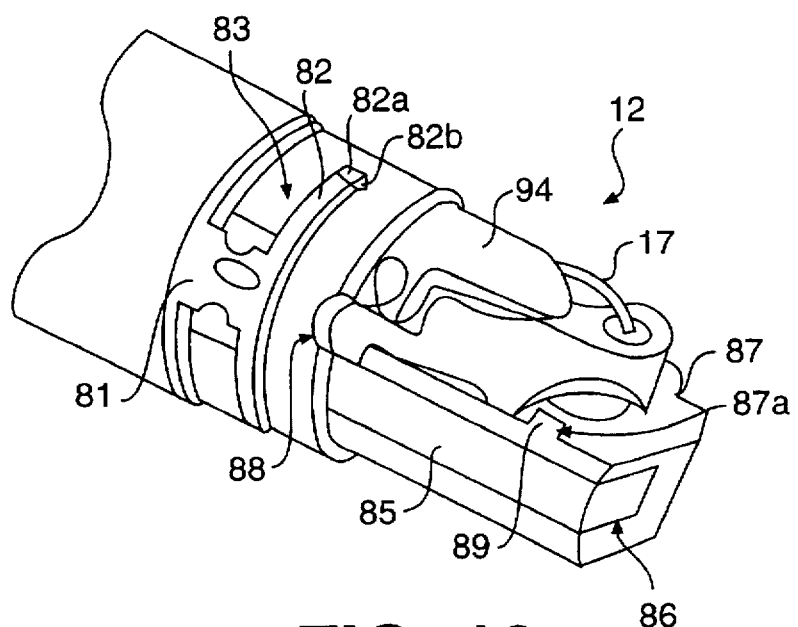
FIG. 12 is a perspective view when the endoscope in FIG. 11 is viewed from the lid side.
Figure 13A:
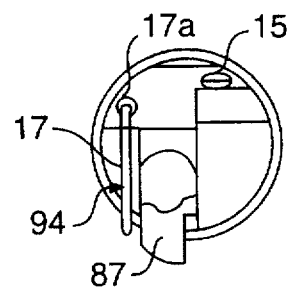
FIG. 13A is a sectional view showing another structure of wire entry prevention means.
Figure 13B:
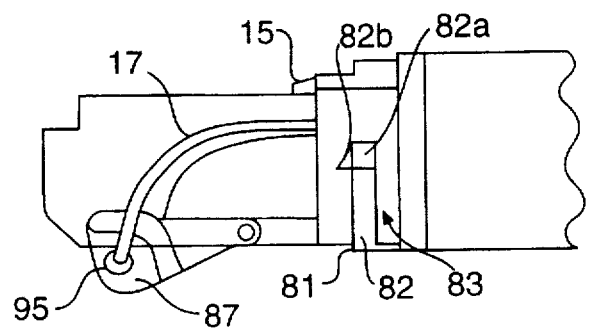
FIG. 13B is a side view of thereof.

As shown in FIG. 12, after a light guide (not shown) is disposed at a predetermined position of the tip component part 21, a lid 85 to close the disposition part is attached to the tip component part 21 where the lock ring 81 having the first slope part 82a and the second slope part 82b made at the lock projection 82 is disposed. The tip of the lid 85 is chamfered matching a chamfer 86 formed at the tip of the tip component part 21.

The lock ring 81 is formed with a relief part 88 for relieving the root of a forceps stand 87 so as not to interfere with motion of the forceps stand 87 while it is made 1.5 mm or more wide to prevent high-frequency leakage.

Figure 14:
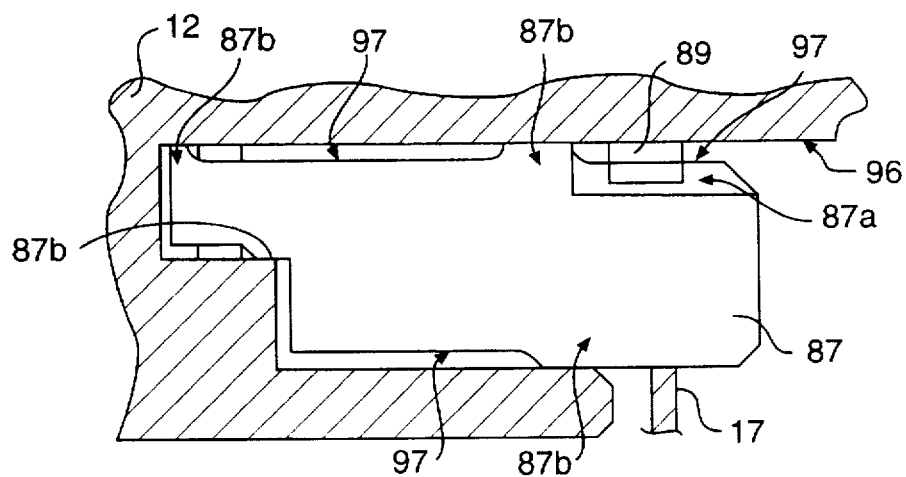
FIG. 14 is a drawing showing the endoscope for improving the cleaning property of the tip component part.

By the way, as shown in FIG. 12, a stopper 89 for regulating the rotation range is integral with the tip component part 21 of the third embodiment so that the forceps stand 87 stops without making a gap open more than the diameter of a manipulation wire 17 between the forceps stand 87 and the forceps stand guide wall 94 when the forceps stand 87 is moved in the downward direction of the tip component part 21 as shown in FIG. 14. On the other hand, a notch 87a is made in the forceps stand 87 at a position corresponding to the stopper 89.

The projection of the stopper 89 is set about 0.5 mm high so as not to adversely affect the cleaning property. The notch 87a is made slightly deeper than the projection height of the stopper 89 and is set to a depth dimension for the forceps stand 87 to stop at a predetermined position when it abuts the stopper 89.

Thus, when the forceps stand 87 is moved in the downward direction of the tip component part 21, the notch 87a of the forceps stand 87 abuts the stopper 89 and the forceps stand 87 stops at a predetermined position where a gap more than the diameter of the manipulation wire 17 does not open between the forceps stand 87 and the forceps stand guide wall 94.

A shaft 95 for coupling the manipulation wire 17 and the forceps stand 87 allows the forceps stand 87 to be removed from the tip component part 21 when the forceps stand 87 is depressed to a position at which it abuts the stopper 89, whereby even if the manipulation wire 17 is damaged, for example, cut or buckled, it can be easily replaced without removing the forceps stand 87.

As shown in FIG. 14, gaps 97 are provided to improve the cleaning property of a slide face 96 of the forceps stand 87 and the tip component part 21. Since there is a fear of occurrence of looseness when the forceps stand 87 is rotated as the gaps 97 are provided, fit face parts 87b are located on both sides of the forceps stand 87 to prevent the looseness.

Figure 16:
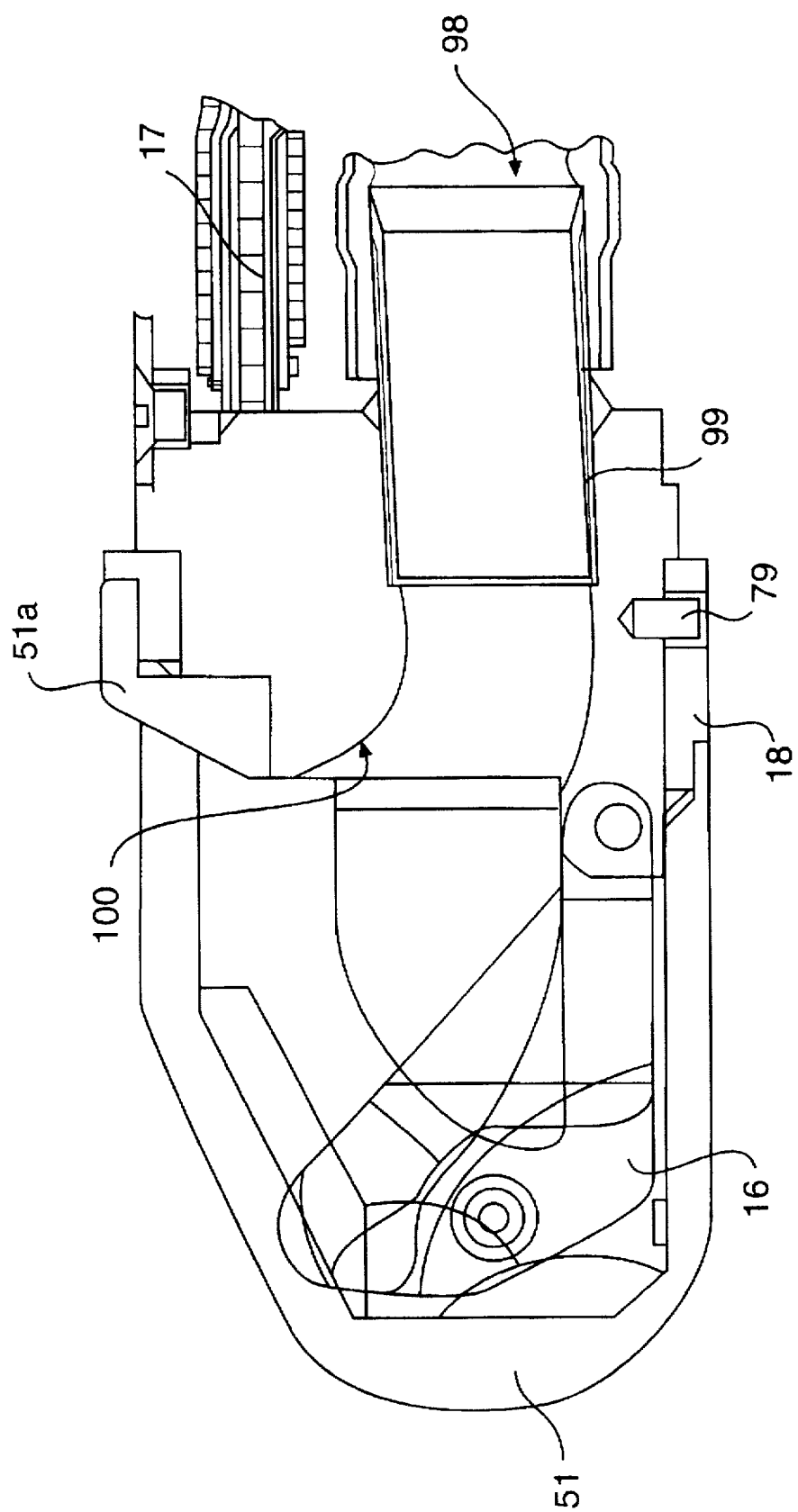
FIG. 16 is a sectional view showing the structure of a forceps channel in the endoscope tip end section.

Further, as shown in FIG. 16, a forceps channel 98 inserted through the tip component part 21, for example, shown in the above-mentioned embodiment is fixed to the tip component part 21 via a pipe 99 in water-sealing relation. The tip side of the pipe 99 is formed with a guide 100 for smoothly bending a treatment tool (not shown) in a desired direction when the forceps stand 16 is raised. The guide 100 has a small curvature on the operator side and a larger curvature as it goes to the tip side, thereby preventing a buckle caused when a treatment tool inserted through the forceps stand 98 is largely bent in a comparatively less flexible part and stabilizing the raising angle.

An insulation part 51a integral with the tip cover 51 is disposed above the guide 100. It is located at a position slightly backward from the guide 100, and is not shaved as the treatment tool is inserted or removed. To fix the lock ring 18 to the tip component part 21 integrally, a pin 79 is stricken into the lock ring 18, which is bonded and fixed to the tip component part 21.

Figure 17:
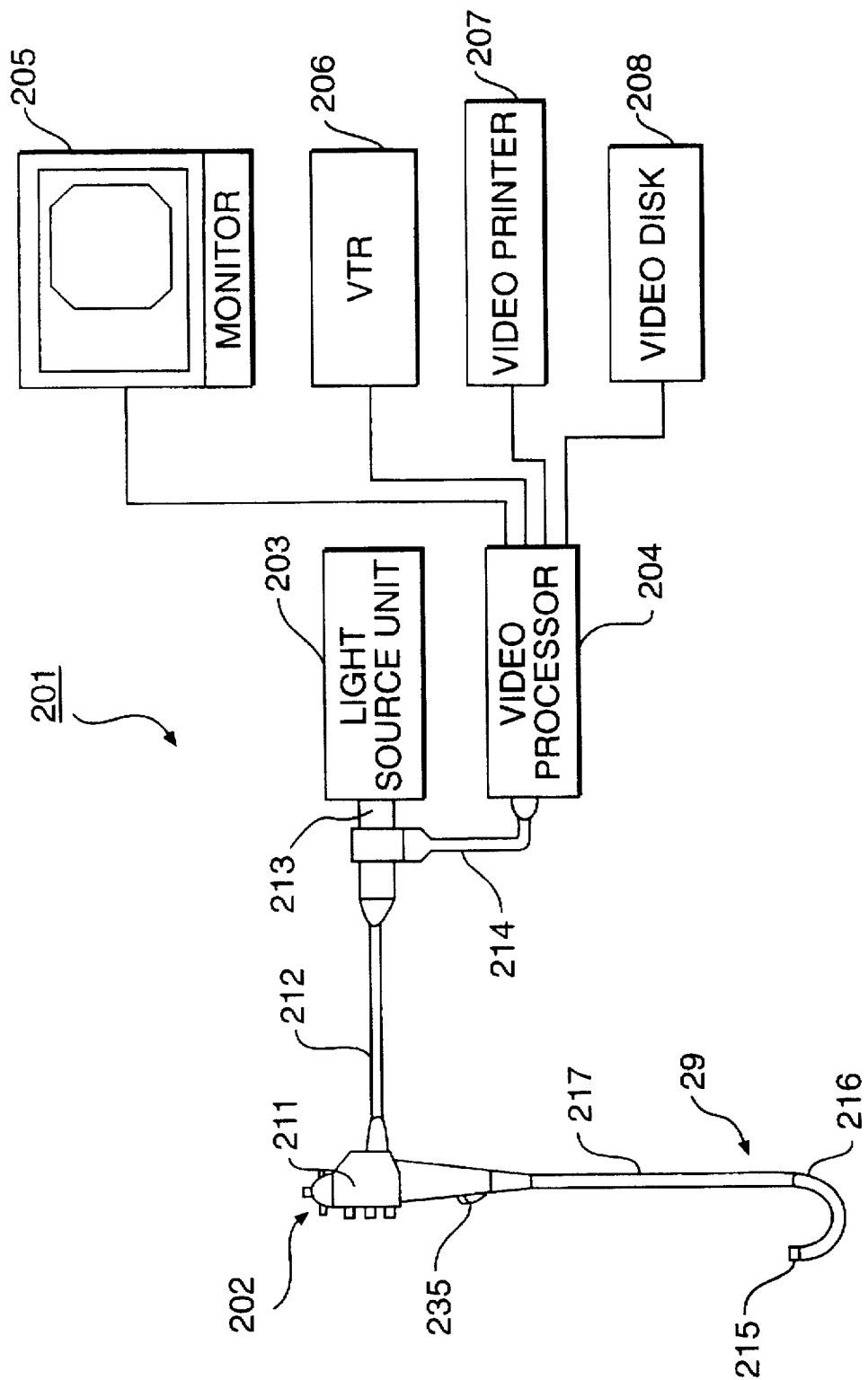
FIG. 17 is an illustration showing the entire configuration of an endoscope system according to a fourth embodiment of the invention.
Figure 18:
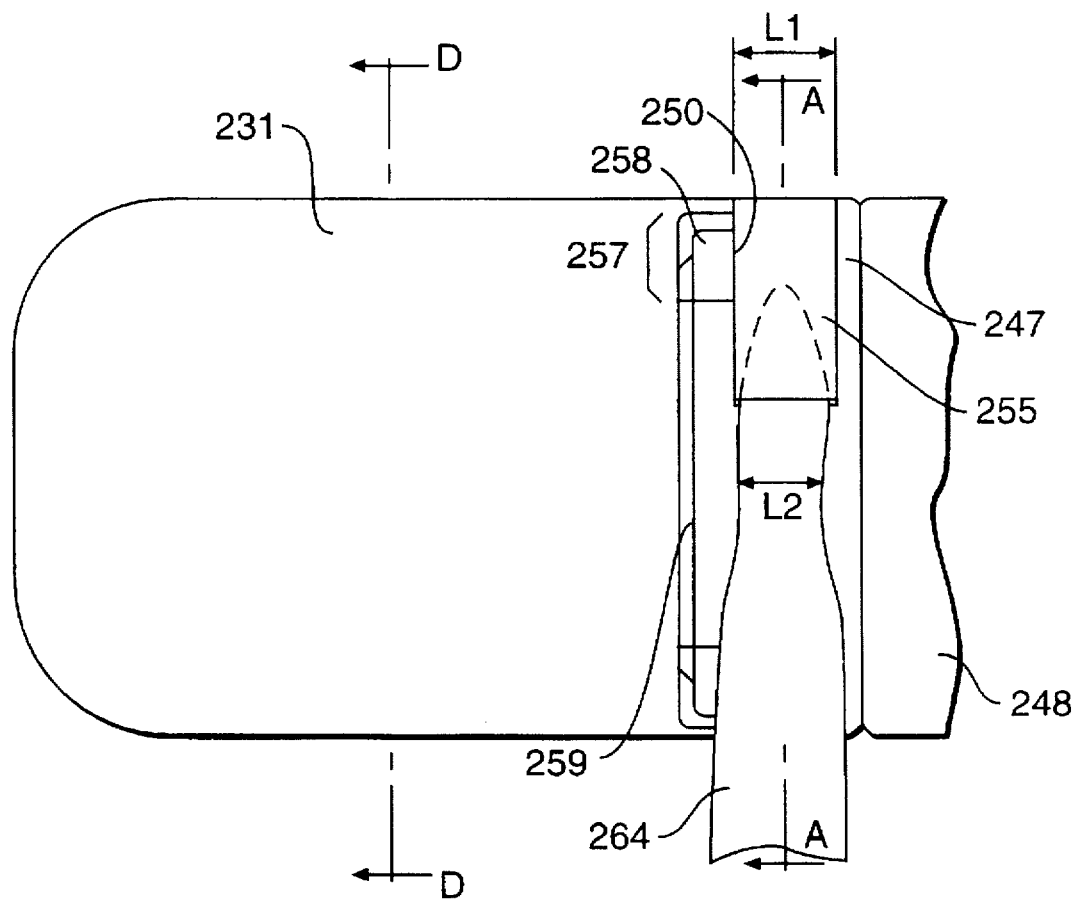
FIG. 18 is a bottom view showing how a tip cover for covering a tip component part is removed with a removal jig in the fourth embodiment of the invention.
Figure 22:
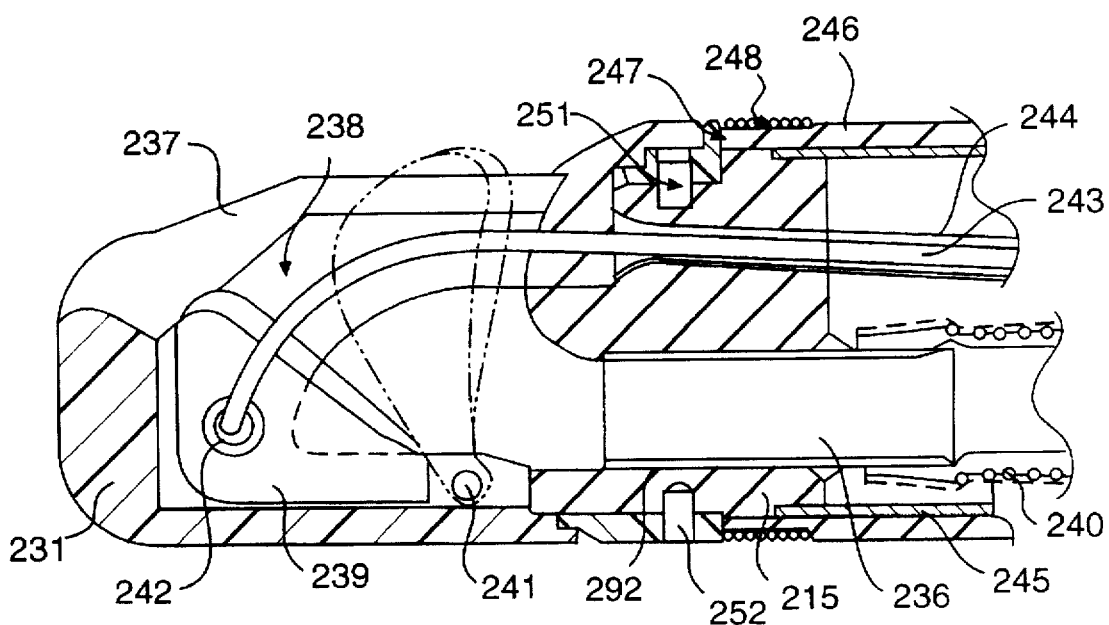
FIG. 22 is a sectional view taken on line C—C in FIG. 19B.
Figure 23:
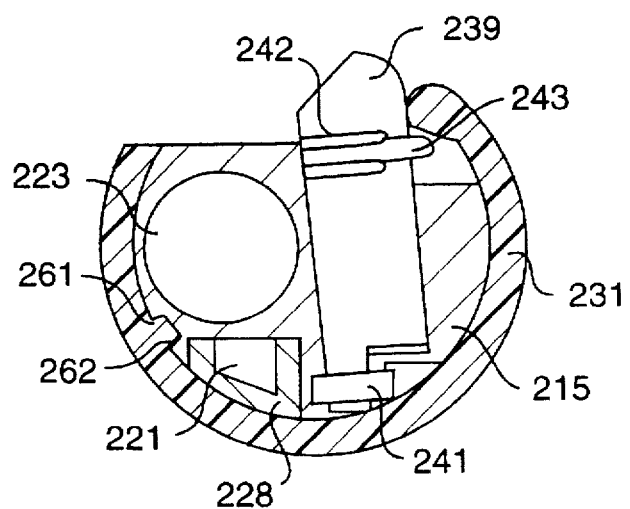
FIG. 23 is a sectional view taken on line D—D in FIG. 18.
Figure 24A:
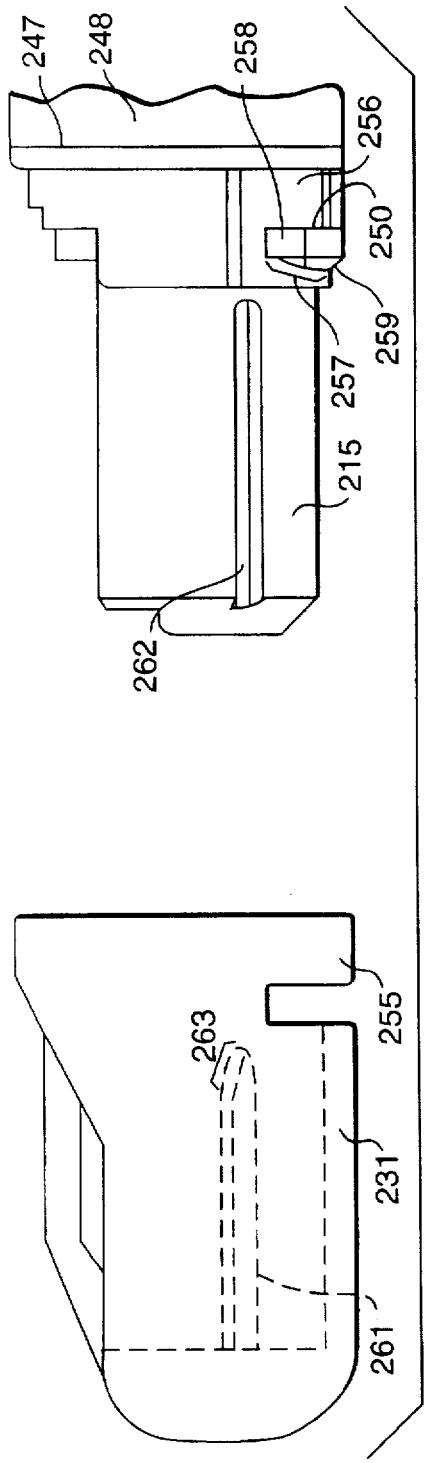
FIGS. 24A and 24B are a side view and a bottom view, respectively, with the tip cover and the tip component part separated before attachment.
Figure 24B:
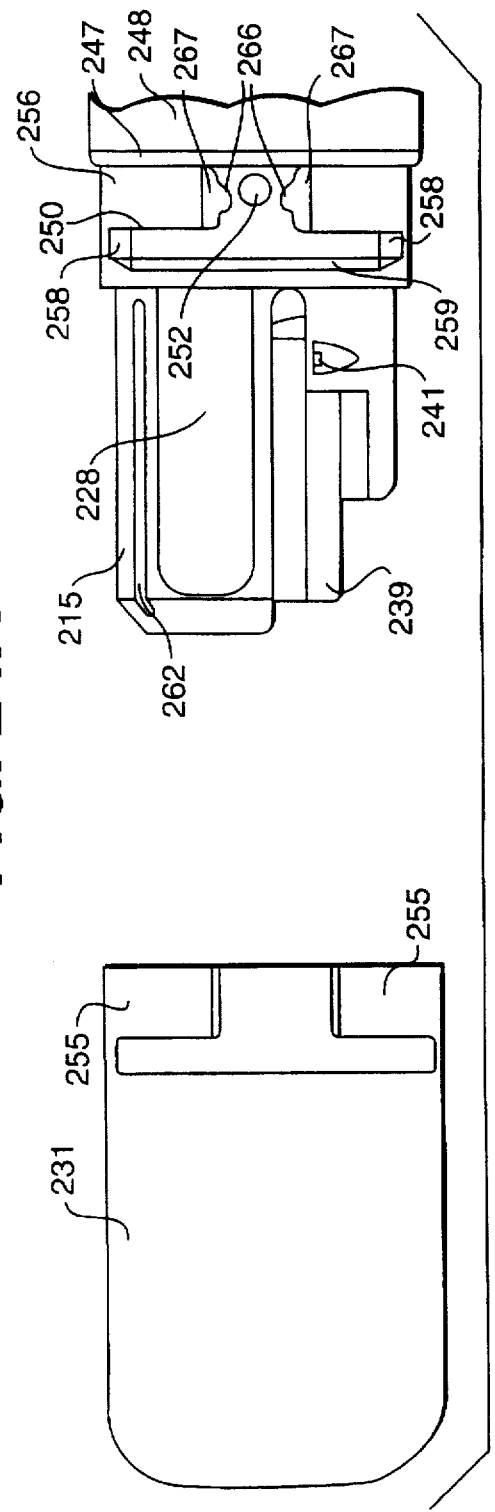
Figure 25A:
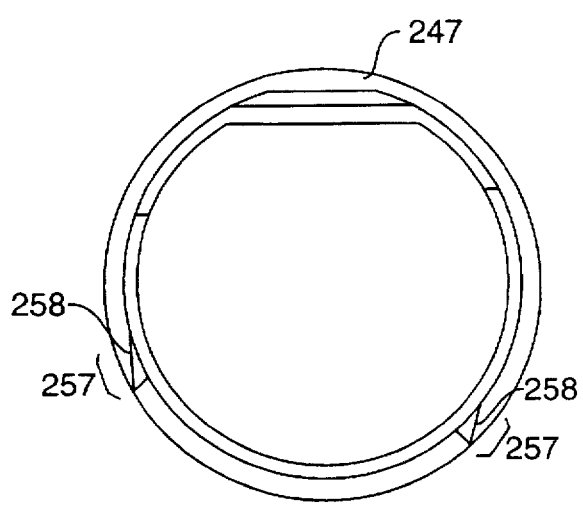
FIGS. 25A and 25B are a front view and a side view, respectively, of a ring.
Figure 25B:
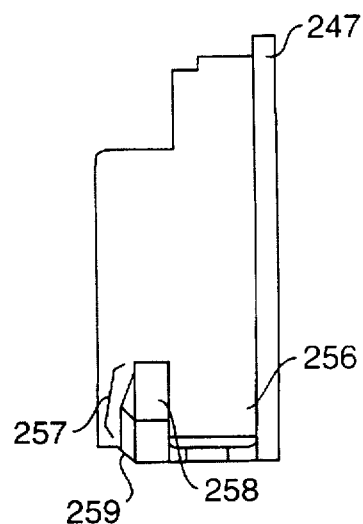
Figure 26A:
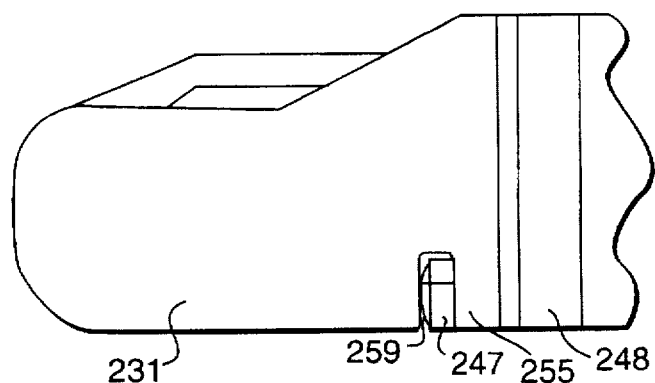
FIGS. 26A and 26B are a side view and a bottom view, respectively, showing an attachment state of the tip cover to the tip component part.
Figure 26B:
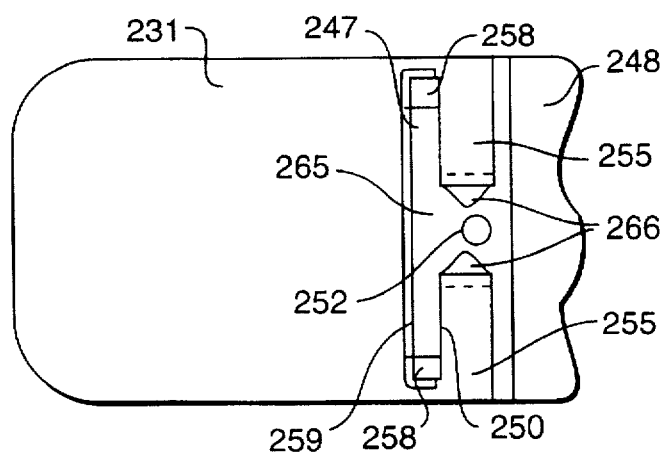
Figure 27:
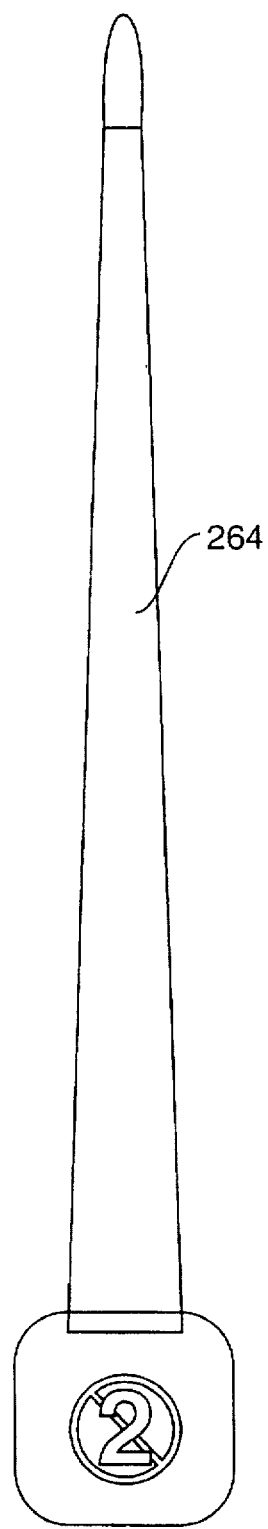
FIG. 27 is an external view of a removal jig.

Fourth embodiment:

FIG. 17 shows the entire configuration of an endoscope system according to a fourth embodiment of the invention. FIG. 18 shows a tip cover for covering a tip component part in the fourth embodiment of the invention. FIG. 19 is a sectional view taken on line A—A in FIG. 18. FIG. 20 is a sectional view taken on line B—B in FIG. 19(B). FIG. 21 shows a molded part of the tip of a light guide fiber in the fourth embodiment of the invention. FIG. 22 is a sectional view taken on line C—C in FIG. 19(B). FIG. 23 is a sectional view taken on line D—D in FIG. 18. FIG. 24 shows the tip cover and the tip component part before attachment in the fourth embodiment of the invention. FIG. 25 is a front view and a side view of a ring in the fourth embodiment of the invention. FIG. 26 shows an attachment state of the tip cover to the tip component part in the fourth embodiment of the invention. FIG. 27 is an external view of a removal jig in the fourth embodiment of the invention.

As shown in FIG. 17, an endoscope system 201 comprises an electronic endoscope 202 in the fourth embodiment of the invention containing image pickup means, a light source unit 203 for supplying illuminating light to the electronic endoscope 202, a video processor 204 containing signal processing means for performing a signal processing for the image pickup means, a monitor 205 for displaying an endoscope image provided by a video signal produced by the video processor 204, a VTR deck 206 for recording and reproducing the video signal, a video printer 207 for making a hard copy of the endoscope image in response to the video signal, and a video disk 208 of a mass storage device for recording the video signal.

The electronic endoscope 202 has an elongated insertion section 209, a manipulation part 211 disposed at the rear end of the insertion section 209, and a universal cable 212 extending from the manipulation part 211 to the outside. The universal cable 212 is provided at the termination with a connector 213, which is connected to the light source unit 203 detachably. A connector disposed on one end of a scope cable 214 is connected to the connector 213 and a connector disposed on the other end is connected to the video processor 204 detachably.

The insertion section 209 comprises a tip component part 215 disposed at the tip, a curved part 216 which is formed at the rear end of the tip component part 215 and can be curved, and a long flexible part 217 extending from the rear end of the curved part 216 to the front end of the manipulation part 211.

As shown in FIG. 20, a light guide fiber 221 for transmitting illuminating light is inserted into the insertion section 209. It is furthermore inserted through the manipulation part 211 and the universal cable 212 to a light guide connector of the connector 213.

Illuminating light is supplied to the light guide connector from the light source unit 203 and is transmitted through the light guide fiber 221. As shown in FIG. 20, the light guide fiber 221 is curved at the tip component part 215 and the illuminating light is transmitted from the fixed tip face through an illuminating lens 222 to the side perpendicular to the longitudinal direction of the insertion section 209 (upward in FIG. 20) for illuminating an object such as the affected part.

An observation window is formed adjoining an illumination window to which the illumination lens 222 is fitted. Fitted to the observation window are a first object lens 223a, a prism 223b, and an object following group lens system 223c making up an object optical system 223 for forming an object image.

A solid state image sensor 224 containing solid state image sensing devices such as CCDs (not shown) is placed at an image formation position of the object optical system 223 for executing photoelectric conversion of an optical image. It is connected to a signal line inserted into the insertion section 209, etc. The signal line is furthermore inserted into the scope cable 214 from the connector 213 and is connected to the video processor 204.

The solid state image sensor 224 has a metal shield frame 225 high in thermal conductivity for covering the solid state image sensing devices such as CCDs, electronic parts such as ICs and capacitors, circuit boards, etc., contained therein, and the inside of the shield frame 225 is filled with radiation silicone (not shown). The components of the solid state image sensor 224 is covered with the shield frame 225, thereby suppressing noise entering the solid state image sensing devices such as CCDs and radiating to the outside and enhancing the heat dissipation function for suppressing heat noise occurrence and preventing degradation by heat of the solid state image sensing devices.

The tip component part 215 is provided with an air and water sending nozzle 226 whose tip is opposed to the observation window, and an air and water sending tube 227 defining an air and water sending channel is fixed to the base end of the air and water sending nozzle 226; even if the outer surface of the first object lens 223a fitted to the observation window becomes dirty, water and air can be sent thereto for cleaning and providing an observation view field.

Figure 19A:
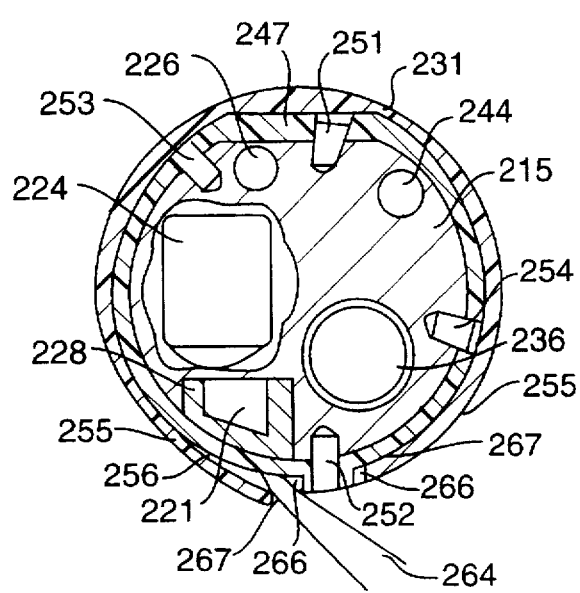
FIGS. 19A, 19B, 19C and 19D are sectional side views taken on line A—A in FIG. 18, each showing different condition of a lock pieces.
Figure 19B:
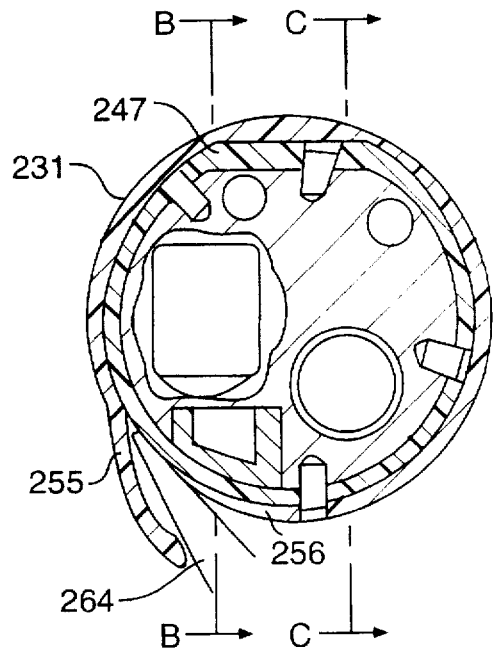
Figure 19C:
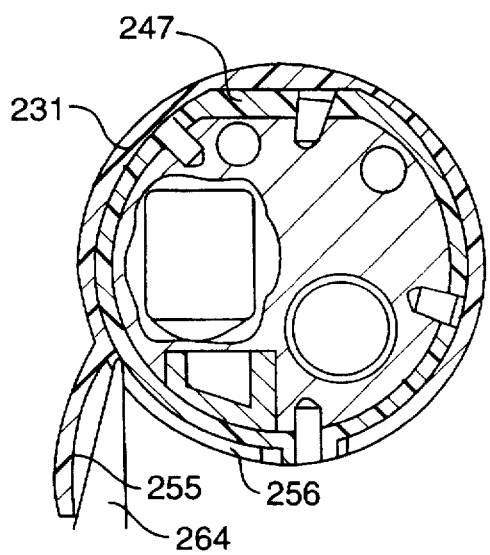
Figure 19D:
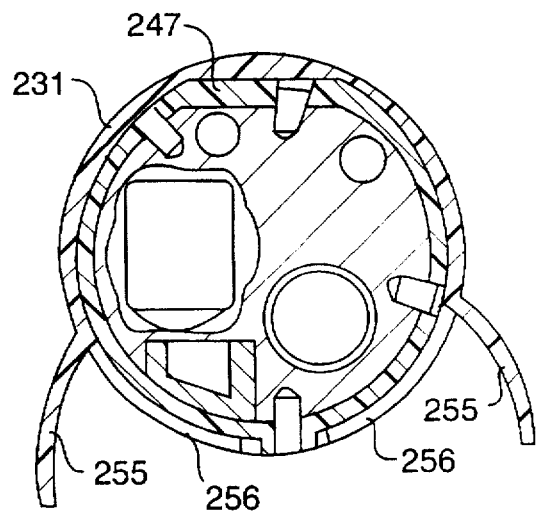
Figure 20:
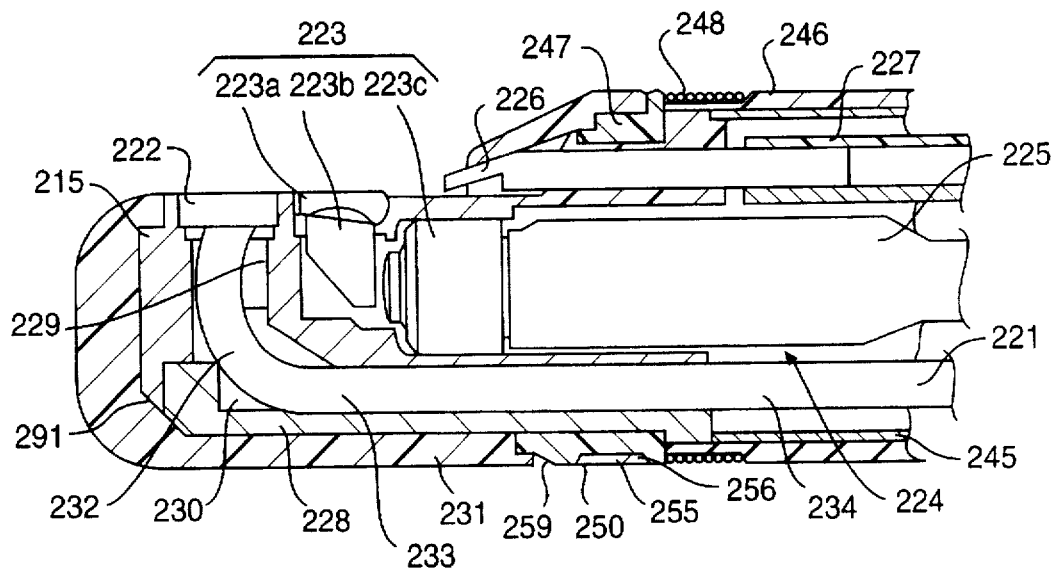
FIG. 20 is a sectional view taken on line B—B in FIG. 19(B)
Figure 21A:
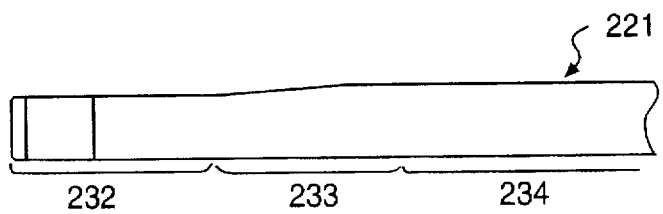
FIG. 21A is a plan view of the tip of the light guide fiber.
Figure 21B:
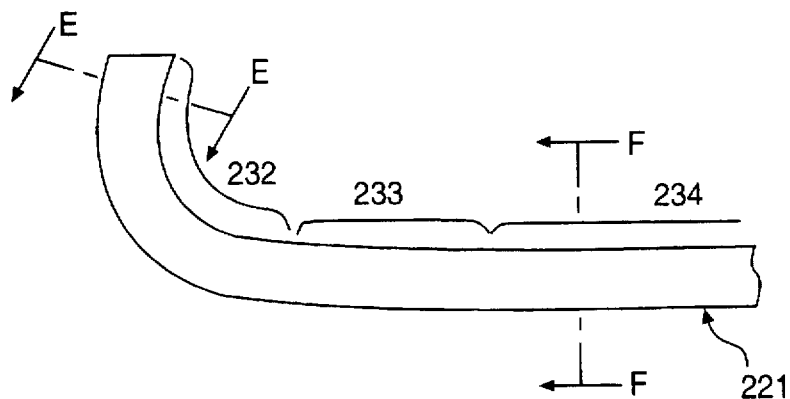
FIG. 21B is a side view of the tip.
Figure 21C:
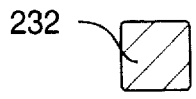
FIGS. 21C and 21D are sectional views taken on line E—E and line F—F in FIG. 21B.
Figure 21D:

As shown in FIGS. 19A, 19B and 20, the tip side of the light guide fiber 221 is placed in a light guide lid 228 below the object optical system 223 and is bent outside the object optical system 223 so that the tip face is directed to the side. Further, it is placed in a hole 229 opened to the side made in the tip component part 215. As shown in FIG. 19, the inside of the light guide lid 228 shaped like ⊃ (or U) in cross section is filled with an adhesive 230 (see FIG. 20) for fixedly securing the tip side of the light guide fiber 221 to the tip component part 215. In FIG. 19, all parts are denoted by reference numerals only in (A) and only main parts are denoted by reference numerals in (B)–(D).

The tip component part 215 has it surroundings covered with a detachable (or replaceable) tip cover 231. As shown in FIG. 19, the light guide lid 228 has its low side shaped like a circular arc and covered with the tip cover 231. It has its tip side formed like a conical shape 291 so as to make a large R form of the tip of the tip cover 231. The hole 229 where a molded part 232 of the tip of the light guide fiber 221 is shaped like a circle.

FIG. 21 shows the molded part 232 of the tip of the light guide fiber 221. FIG. 21(A) is a plan view of the tip of the light guide fiber 221. FIG. 21(B) is a side view of the tip. FIGS. 21(C) and (D) are sectional views taken on line E—E and line F—F in FIG. 21(B). As shown in FIGS. 21(A) and (B), the bent part of the tip of the light guide fiber 221 is formed with the molded part 232 like a square in cross section shown in FIG. (C). The rear end of the molded part 232 leads via a transition part 233 with a gradually lowering fiber filling ratio to a soft part 234 of a small filling ratio shaped substantially like a rectangle in cross section shown in FIG. 21(D). The transition part 233 is formed in an axial direction of the insertion section 209.

As shown in FIG. 17, a treatment tool insertion inlet (or forceps insertion slot) 235 for inserting a treatment tool such as forceps is made in the vicinity of the tip of the manipulation part 211, and communicates with a treatment tool channel (or forceps channel) 236 inside the insertion section 209.

The forceps channel 236 is formed in an axial direction of the insertion section 209 and branches to two ways in the vicinity of the tip of the manipulation part 211; one communicates with the forceps insertion slot 235 and the other is inserted into the universal cable via a suction manipulation mechanism and is connected to a suction device via a suction mouthpiece (not shown) of the connector 213. This means that the forceps channel 236 is also used as a suction channel. It is formed of a channel tube 240, which is connected at the tip to the rear end projecting backward of the channel mouthpiece 292 fixedly secured to the tip component part 215 with an adhesive as shown in FIG. 22.

As shown in the figure, a recess 237 opened sideway is made in the tip cover 231 for covering the tip component part 215 before the tip opening of the forceps channel 236. A forceps raising stand 239 for forming a forceps raising mechanism 238 for guiding a treatment tool, etc., inserted into the forceps channel 236 to the object such as the affected part is placed in the recess 237. The base end of the forceps raising stand 239 is supported by a raising shaft 241 for rotation. The raising shaft 241 is also shown in FIG. 23.

The tip of a raising wire 243 for performing raising manipulation is fixed to the tip of the forceps raising stand 239 by a wire fixing member 242; for example, the forceps raising stand 239 can be raised as shown by the phantom line from the solid line in FIG. 22 by moving the raising wire 243 in such a manner of pulling it backward.

The raising wire 243 is inserted into a wire channel 244 defined in the insertion section 209 and is connected at the rear end to a raising manipulation lever (not shown) of the manipulation part 211. The raising manipulation lever can be turned, etc., for pushing and pulling the raising wire 243 for rotating the forceps raising stand on the raising shaft 241 for controlling the raising angle of the forceps raising stand 239.

The raising angle of the forceps raising stand 239 is controlled, whereby the stem on the tip side of the forceps projecting from the tip opening of the forceps channel 236 is pushed by a slope of the forceps raising stand 239 for regulating the projecting direction and guiding in a desired direction.

As shown in FIGS. 20 and 22, the tip of a curved frame 245 at the extreme tip forming the curved part 216 that can be curved is fixedly secured to the rear end of the tip component part 215, and a curved frame at the following stage (not shown) is connected pivotably to the rear end of the curved frame 245 by a rivet, etc. The curved frame 245 has its outer peripheral surface covered with tube-shaped curved rubber 246 rich in flexibility as a protection member for protecting the curved part 216.

The manipulation part 211 is provided with an angle knob (not shown) for curving the curved part 216 and curving manipulation of the angle knob is transmitted by an angle wire (not shown), which is fixedly secured to the tip component part 215 or the curved frame 245 at the extreme tip.

The tip of the curved rubber 246 is brought into intimate contact with a ring 247 made of an insulation member such as polysulfone fitted to the tip component part 215 and is fixed by bobbin winding bonding 248.

As shown in FIG. 19, the ring 247 is fixed to the tip component part 215 by four removal prevention pines 251, 252, 253, and 254. The pins 251 and 252 disposed in thick parts are made of metal and the pins 253 and 254 disposed in thin parts are made of plastic.

The ring 247 is formed with grooves 256 for locking lock pieces 255 of the tip cover 231 as described below. The lock pieces 255 are locked into the grooves 256 for reliably fixing the tip cover 231. They are place outside the grooves 256 with a removal jig 264 and bent outward in the vicinity of the root of each lock piece 255, thereby releasing engagement with the grooves 256, whereby the tip cover 231 can be easily removed from the tip component part 215. The jig 264 is inserted into a gap defined between the lock pieces 255 and the ring in the tangent direction of the lock pieces 255. Since the lock pieces 255 are plastically deformed at the removal time, the tip cover 231 cannot again be attached to the tip component part 215 for reuse for endoscope test.

FIG. 24 is a side view (strictly, a side view from an upward direction slightly from a side direction) and a bottom view with the tip cover 231 and the tip component part 215 separated before attachment.

The tip cover 231 made of polysulfone, etc., shown on the right of FIG. 24 is attached to the tip component part 215 shown on the right of FIG. 24 detachably from the tip side. The rear end of the tip cover 231 is opened and is formed with a pair of lock pieces 255 circumferentially. The total length of the two lock pieces 255 is a half or less of the full circumference of the tip cover 231, and the thickness is 0.4 mm. The ring 247 fixed to the tip component part 214 is formed with the grooves 247 circumferentially. The lock pieces 255 are wrapped in the grooves 256 and with steps 250 of the grooves 256 for preventing removal, the tip cover 231 is attached to the tip component part 215. FIG. 25 is a front view and a side view of the ring 247.

A slope 258 is formed at an end 257 of the groove 256 made in the circumferential direction of the ring 247 and a slope 259 is also formed on the periphery of the front of the groove 256. The lock pieces 255 of the tip cover 231 inserted from the tip are widened by the slopes 258 and 259 and fitted into the grooves 256 and the steps 250 on the rear thereof provide a removal prevention function of the tip cover 231 for reliably fixing it.

As shown in FIG. 24, to attach the tip cover 231, while a guide 261 disposed on the tip cover 231 is inserted into a guide groove 262 made in the tip component part 215, the tip cover 231 is inserted. At this time, the end of the guide 261 is formed with a taper 263 to facilitate insertion into the guide groove 262. The guide 261 and the guide groove 262 also serve as a rotation prevention function of the tip component part 215.

The ring 247, which is attached and detached again and again, has resistance to repeated attachment and detachment. Thus, it is formed of a harder material than the tip cover 231 with glass mixed into plastic such as polysulfone. To remove the tip cover 231, the removal jig 264 is used. FIG. 26 shows an attachment state of the tip cover 231 to the tip component part 215. FIG. 27 is an external view of the removal jig 264.

As shown in FIG. 26, reliefs 266 for inserting the removal jig 264 are made at a thick portion 265 formed on the ring 247 adjoining the tip proximity of each attached lock piece 255. As shown in FIGS. 19A and 24, a gap 267 is made between the tip of each lock piece 255 and the ring 247 for facilitating removal of the lock pieces 255 with the removal jig 264. Next, a removal method of the tip cover 231 will be described:

a) Using the reliefs 266 and the gaps 267, insert the removal jig 264 into the lower part of the tip of one lock piece 255, as shown in FIG. 19(A).

b) Further, insert the removal jig 264 to the root of the lock piece 255 along the groove 256 of the ring 247, as shown in FIG. 19(B).

c) Upon insertion of the removal jig 264 to the root of the lock piece 255, pinch the lock piece 255 between a finer and the removal jig 264, bend the lock piece 255, and plastically deform it for releasing engagement with the groove 256, as shown in FIG. 19(C).

d) Perform a) to c) also for the other lock piece 255, as shown in FIG. 19(D).

be) Check that both the lock pieces 255 are sufficiently bent, then pull the tip cover 231 forward of the tip component part 215 to remove the former from the latter.

Thus, the attached tip cover 231 can be easily removed by using the removal jig 264.

In the removing step of the tip cover 231, the removal jig 264 is pushed against the ring 247 each time the tip cover 231 is removed. The removal jig 264 is made of a material such as acrylic softer than the tip cover 231 and the ring 247 to make the grooves 256 of the ring 247 hard to scratch. In other words, they are made of harder material in the order of the ring 247, the tip cover 231, and the removal jig 264.

As shown in FIG. 18, width L2 in the vicinity of the tip of the removal jig 264 is made smaller than width L1 of the groove 256 so that the removal jig 264 can be inserted into the groove 256.

If the tip cover 231 is removed in such a manner as described above, once it is removed, the tip cover 231 cannot again be attached because the lock pieces 255 are bent and plastically deformed. Therefore, whenever the tip cover 231 is removed, a new, clean, and sterilized tip cover 231 will be attached and cleaning labor of the tip cover 231 and the infection chance among patients can be decreased. Also, the tip cover 231 can be easily removed by using the removal jig 264.

Figure 29A:
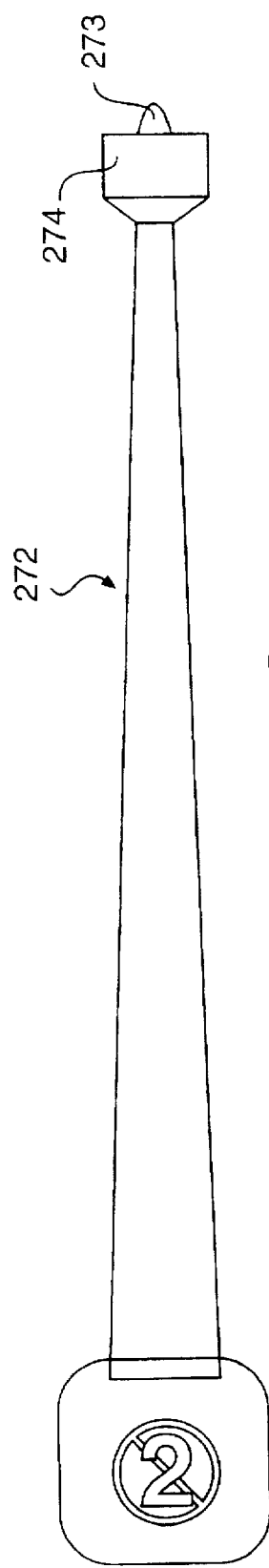
FIGS. 29A, 29B and 29C are a plan view, side view, and front view, respectively, showing the removal jig.
Figure 29B:
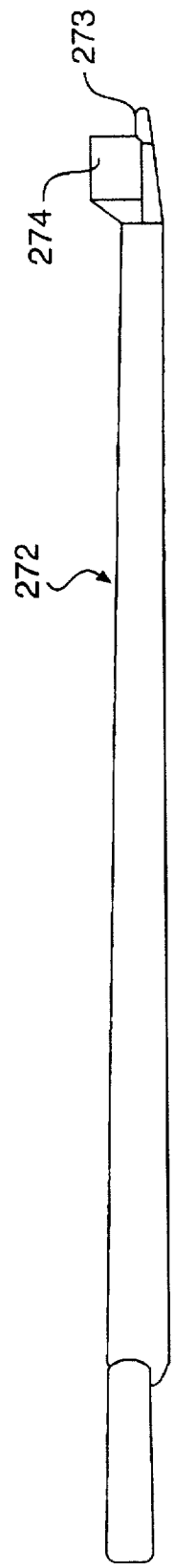
Figure 29C:
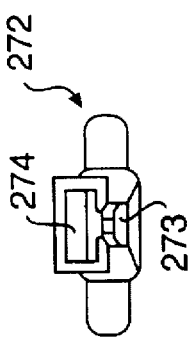
Figure 30:
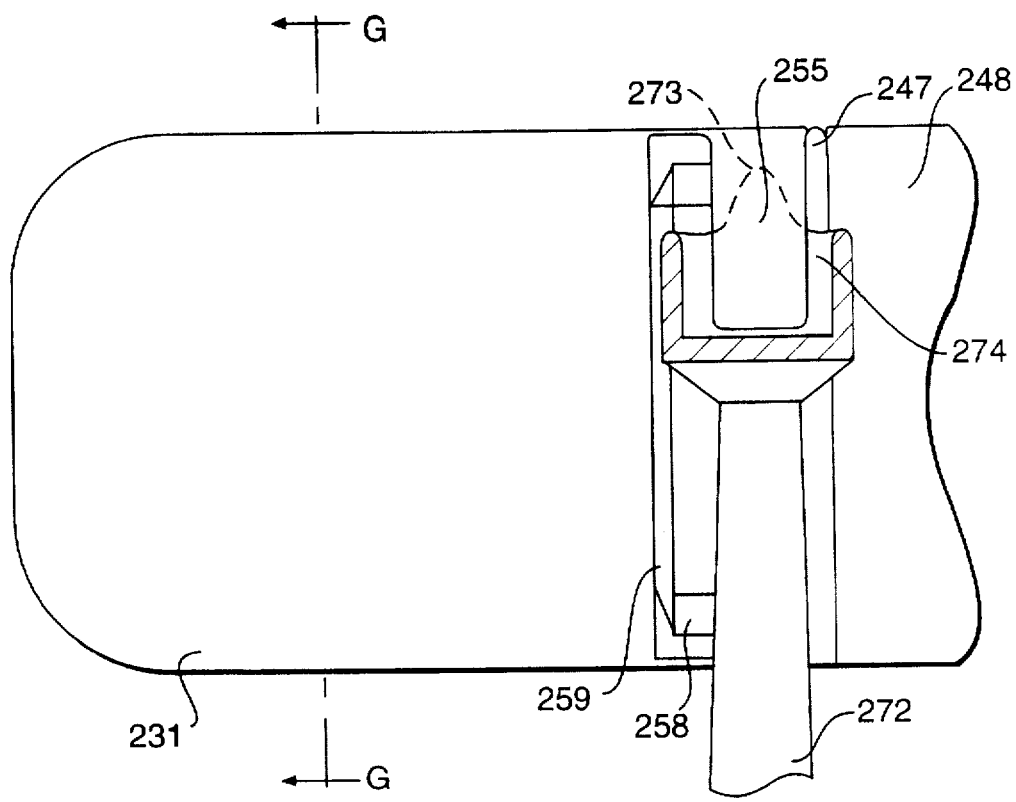
FIG. 30 is a bottom view showing how the tip cover for covering the tip component part is removed with the removal jig.
Figure 31:
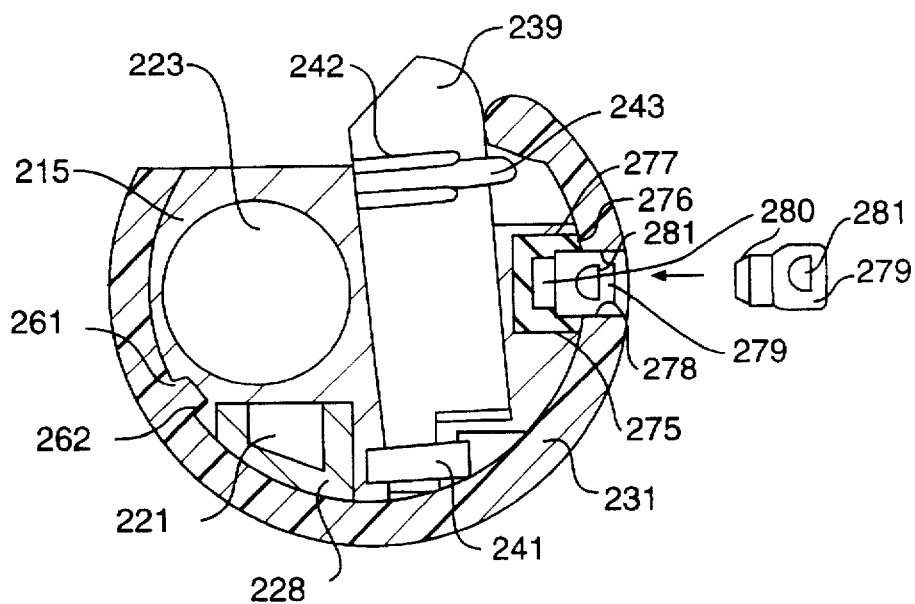
FIG. 31 is a sectional side view taken on line G—G in FIG. 30.
Figure 32A:
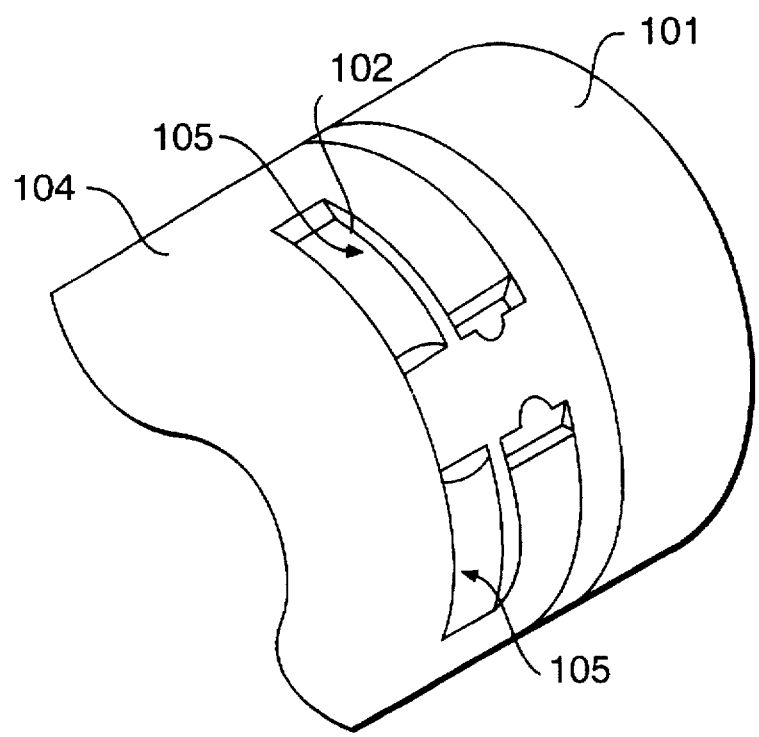
FIGS. 32A and 32B are a perspective view and a sectional view, respectively, showing a state in which a tip cover is attached to an endoscope tip end section in a conventional example.
Figure 32B:
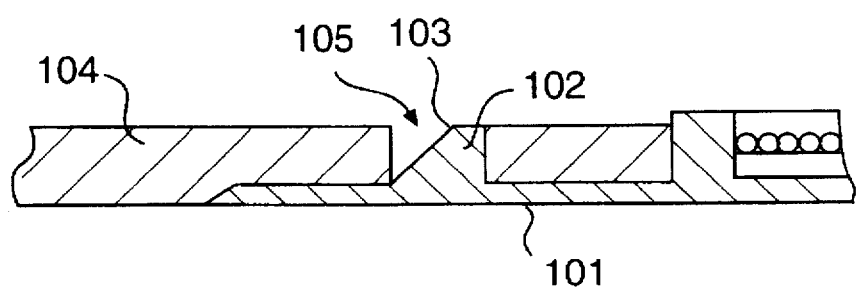
Figure 33:
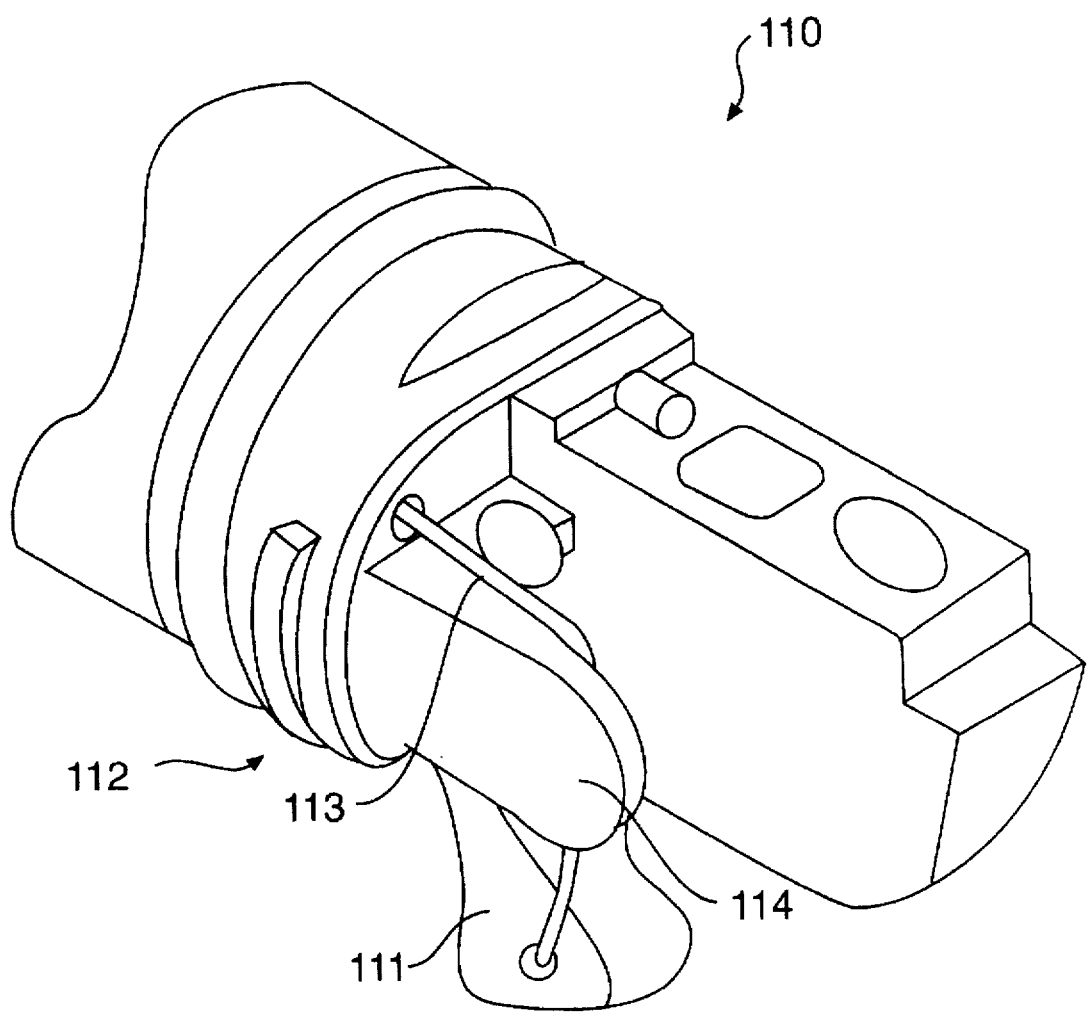
FIG. 33 is a perspective view showing the positional relationship between a manipulation wire and forceps.

Fifth embodiment:

FIG. 28 is a sectional view showing a tip component part to which a tip cover is attached according to a fifth embodiment of the invention. FIG. 29 shows the form of a removal jig in the fifth embodiment of the invention. FIG. 30 shows how the tip cover attached to the tip component part is removed with the removal jig in the fifth embodiment of the invention. FIG. 31 is a sectional view taken on line G—G in FIG. 30.

As shown in FIG. 28, in the fifth embodiment of the invention, a thick portion 265 of a ring 247 located at the tip proximity of a lock piece 255 is formed with a slope 271 toward a groove 256 for facilitating insertion of a removal jig 272 along the slope 271. In FIG. 28, all parts are denoted by reference numerals only in (A) and only main parts are denoted by reference numerals in (B).

As shown in FIG. 29, a tip 273 of the removal jig 272 is provided with a box 274. As shown in FIG. 30, the internal width of the box 274 is lager than the width of the lock piece 255 so that the tip of the lock piece 255 fits in the box 274.

As shown in FIG. 31, a cylindrical rubber member 277 formed with a projection 276 on an internal face is fitted into a hole 275 made in a side face of a tip component part 215. After a tip cover 231 is attached, a flange 280 disposed in a pin 279 through a hole 278 of the tip cover 231 to the cylindrical rubber member 277 is fixed by the projection 276 in the rubber member 277 and the pin 279 prevents removal of the tip cover 231. The phantom line in FIG. 31 indicates the pin 279 before fixture and when the pin 279 is pushed as indicated by the arrow, it becomes as indicated by the solid line.

Figure 28A:
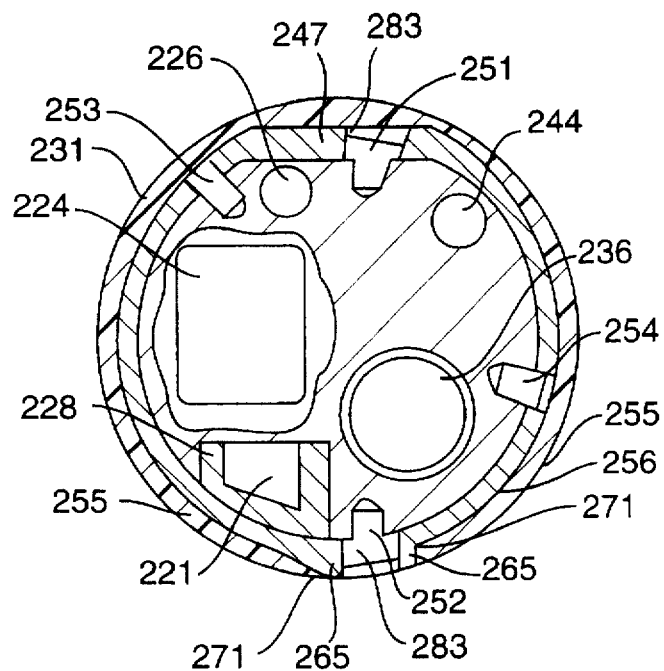
FIG. 28A is a bottom view showing a tip cover and FIG. 28B shows how for covering a tip component part is removed with a removal jig in a fifth embodiment of the invention.
Figure 28B:
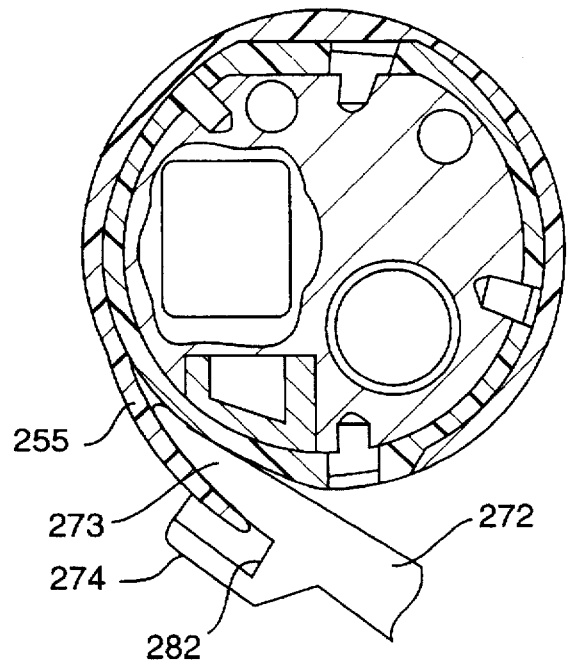

Next, a removal method of the tip cover 231 with the removal jig 272 in the embodiment will be described:

a) Insert the tip 273 of the removal jig 272 into the hole 278 of the tip cover 231, hook the tip 273 of the removal jig 272 in a hook hole 281 of the pin 279, and pull out the pin 279.

b) As shown in FIG. 28(B), insert the tip 273 of the removal jig 272 in the lower part of one lock piece 255 along the slope 271 shown in FIG. 28(A).

c) While inserting the removal jig 272, guide the lock piece 255 until the lock piece 255 strikes an inner wall 282 of the box 274.

d) With the lock piece 255 locked in the groove 256 striking the wall 282 of the box 274, lift up the removal jig 272, bend the lock piece 255, and plastically deform it for releasing engagement with the groove 256.

e) Perform b) to d) also for the other lock piece 255, as shown in FIG. 19(D).

f) Check that both the lock pieces 255 are sufficiently bent, then remove the tip cover 231.

The tip cover 231 can be easily removed from the tip component part 215 in such a manner.

In FIG. 28, a flange 283 is made in the heads of metal pins 251 and 252 of four removal prevention pins 251–254 of the ring 247 to prevent the pins 251 and 252 from sinking too much. The heads of the pins 253 and 254 made of plastic such as polysulfone are shaped like a sphere.

The removal jig 272 is provided with the box 274 as described above, whereby the user can be prevented from a finger injury at the tip of the lock piece 255 or the tip 273 of the removal jig 272.

The fifth embodiment produces similar effects to those of the fourth embodiment in other points.

According to the invention, as described above, there can be provided an endoscope which is good in attachment property of a tip cover to an endoscope tip end section, excellent in insertion property without any step on the outer surface of the attachment part between the tip cover and the endoscope tip end section when the tip cover is attached to the endoscope tip end section, and has a lock mechanism for preventing the tip cover from falling out form the endoscope tip end section.

According to the invention, the endoscope has the detachable tip cover that can be attached to the tip component part by locking the lock pieces disposed in the endoscope tip cover in the grooves made in the tip component part of the endoscope. When the tip cover is removed from the tip component part, the removal jig is used to plastically deform the lock pieces. Thus, the tip cover can be easily removed with the removal jig. Since the removed tip cover has the lock pieces plastically deformed, reuse of the tip cover can be prevented reliably.

What is claimed is:

1. An endoscope comprising:
   an insertion section for inserting into an abdominal cavity of a patient;
   a tip end section disposed at a tip end of said insertion section;
   a manipulation part disposed at a proximal end of said insertion section;
   a lock ring section disposed on said tip end section;
   a tip cover coupled to said tip end section; and
   an engagement mechanism for engaging said tip end section with said tip cover, said engagement mechanism including:
   a first engagement member disposed on said lock ring section, said first engagement member having an engagement projection,
   a second engagement member disposed on said tip cover, said second engagement member having an engagement recess, and
   a slant section disposed on one of said first and second engagement members.

2. The endoscope according to claim 1, wherein said engagement projection is disposed on said lock ring section, said engagement recess is disposed on said tip end cover, and said slant section is disposed on said engagement projection.

3. The endoscope according to claim 2, wherein said slant section is disposed on a circumferential face and longitudinal direction tip side face of the tip end of said engagement projection.

4. The endoscope according to claim 2, wherein said slant projection is formed projecting from engagement projection to the endoscope tip end side.

5. The endoscope according to claim 2, wherein said slant section is formed as a slope rising from the lower face of the tip side to the upper face of the engagement projection.

6. The endoscope according to claim 5, wherein said slant section has 5 mm or less wide.

7. The endoscope according to claim 2, wherein aid second engagement member comprises at least one lock piece having an elasticity, and said lock piece comprises a thin part formed at a root proximity thereof.

8. The endoscope according to claim 7, wherein said first engagement member comprises a lock groove, and said lock piece has an outer form having the length and width dimensions substantially the same as or smaller than those of said lock groove.

9. The endoscope according to claim 7, wherein the outer dimensions of said lock piece are set the same as those of other portions of said tip end cover or to the dimensions not projecting therefrom.

10. The endoscope according to claim 7, wherein said lock piece comprises a hinge having a part formed as a predetermined thickness.

11. The endoscope according to claim 7, wherein aid lock piece is made 1 mm or more wide and 0.5 mm or more thick.

12. The endoscope according to claim 7, wherein an end of said lock piece is formed at the same angle in the range of 45° to 90° with the outer peripheral surface.

13. The endoscope according to claim 7, wherein said lock piece comprises a pair of lock piece members.

14. The endoscope according to claim 2, wherein the outer dimensions of said engagement projection are set the same as those of other portions of said tip end cover.

15. The endoscope according to claim 2, wherein said slant section comprises a first slope part formed on the circumferential face of a tip of said engagement projection and a second slope part formed on the longitudinal direction of the tip side face of the tip of said engagement projection.

16. The endoscope according to claim 1, wherein said lock ring is formed of a material having living body compatibility.

17. The endoscope according to claim 16, wherein said lock ring section is formed of polysulfone.

18. The endoscope according to claim 1, wherein the minimum thickness of said lock ring section is substantially 0.3 mm.

19. The endoscope according to claim 1, wherein said lock ring section is colored a different color from said tip end cover.

20. The endoscope according to claim 1, wherein said slant section is disposed on said second engagement member disposed on said tip end cover.

21. The endoscope according to claim 20, wherein said tip end cover comprising a lock piece having an elasticity and sad slant section comprises a slant recess formed on an inner surface of said lock.

22. The endoscope according to claim 21, wherein said slant recess is formed as a slope declining from the top face side of said first engagement member side toward the bottom face direction of said lock piece.

23. The endoscope according to claim 1, wherein said tip end section comprises a forceps stand for supporting a treatment tool inserting into the endoscope and projecting from the endoscope tip end section, a manipulation wire connected at one end to said forceps stand and coupled at the other end to said manipulation part, and a guide wall for guiding said manipulation wire, and a predetermined gap is defined between said forceps stand and said guide wall.

24. The endoscope according to claim 23, wherein said guide wall comprises a slant surface.

25. The endoscope according to claim 23, wherein said tip end section comprises a stopper for regulating a rotation range of said forceps stand.

26. The endoscope according to claim 25, wherein the projection of said stopper is set substantially 0.5 mm high.

27. The endoscope according to claim 1, wherein said tip end cover comprises a relief part formed on an inner surface thereof.

* * * * *

UNITED STATES PATENT AND TRADEMARK OFFICE
CERTIFICATE OF CORRECTION

PATENT NO. : 5,730,701
DATED : March 24, 1998
INVENTOR(S) : Tatsuya FURUKAWA et al.

It is certified that error appears in the above-identified patent and that said Letters Patent is hereby corrected as shown below:

Column 18, Line 59 change ``aid'' to --said--.

Column 19, Line 8 change ``aid'' to --said--.

Column 20, Line 6 change ``sad'' to --said--.

Signed and Sealed this

Twenty-sixth Day of September, 2000

Attest:

Q. TODD DICKINSON

*Attesting Officer*    *Director of Patents and Trademarks*